(12) United States Patent
Leahy et al.

(10) Patent No.: US 9,737,509 B1
(45) Date of Patent: Aug. 22, 2017

(54) ANTIMICROBIAL COMPOSITIONS, METHODS OF USE, AND METHODS OF TREATMENT OF INFECTIONS

(71) Applicants: James William Leahy, Lutz, FL (US); Dennis Edward Kyle, Lithia, FL (US); Brian Andrew Vesely, Tampa, FL (US); Benjamin Joe Eduful, Tampa, FL (US); Ankush Kanwar, Tampa, FL (US); Linda Corrinne Barbeto, Brandon, FL (US)

(72) Inventors: James William Leahy, Lutz, FL (US); Dennis Edward Kyle, Lithia, FL (US); Brian Andrew Vesely, Tampa, FL (US); Benjamin Joe Eduful, Tampa, FL (US); Ankush Kanwar, Tampa, FL (US); Linda Corrinne Barbeto, Brandon, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/162,698

(22) Filed: May 24, 2016

Related U.S. Application Data

(60) Provisional application No. 62/166,327, filed on May 26, 2015.

(51) Int. Cl.
| | | |
|---|---|---|
| *A61K 31/517* | (2006.01) | |
| *A61K 31/416* | (2006.01) | |
| *A61K 31/437* | (2006.01) | |
| *A61K 31/47* | (2006.01) | |
| *A61K 31/4545* | (2006.01) | |
| *A61K 31/46* | (2006.01) | |

(52) U.S. Cl.
CPC .......... *A61K 31/416* (2013.01); *A61K 31/437* (2013.01); *A61K 31/4545* (2013.01); *A61K 31/46* (2013.01); *A61K 31/47* (2013.01); *A61K 31/517* (2013.01)

(58) Field of Classification Search
CPC ..................................... A61K 31/416
USPC ..................... 514/266.23; 546/119
See application file for complete search history.

(56) References Cited

U.S. PATENT DOCUMENTS

| | | |
|---|---|---|
| 2014/0343037 A1 | 11/2014 | Huang et al. |
| 2015/0051203 A1 | 2/2015 | Chimmanamada et al. |
| 2016/0143884 A1* | 5/2016 | Orlemans ............ A61K 31/403 514/406 |

FOREIGN PATENT DOCUMENTS

WO    2014/025395    * 2/2014

OTHER PUBLICATIONS

International Search Report, dated Aug. 12, 2016, for application No. PCT/US16/33897; Mail Stop PCT, 13 pages.

* cited by examiner

*Primary Examiner* — Shengjun Wang
(74) *Attorney, Agent, or Firm* — Thomas | Horstemeyer, LLP

(57) ABSTRACT

The present disclosure provides compositions including a compound (e.g., compounds A-D), pharmaceutical compositions including the compound, methods of treatment of a condition (e.g., an infection) or disease, methods of treatment using compositions or pharmaceutical compositions, and the like.

5 Claims, 1 Drawing Sheet

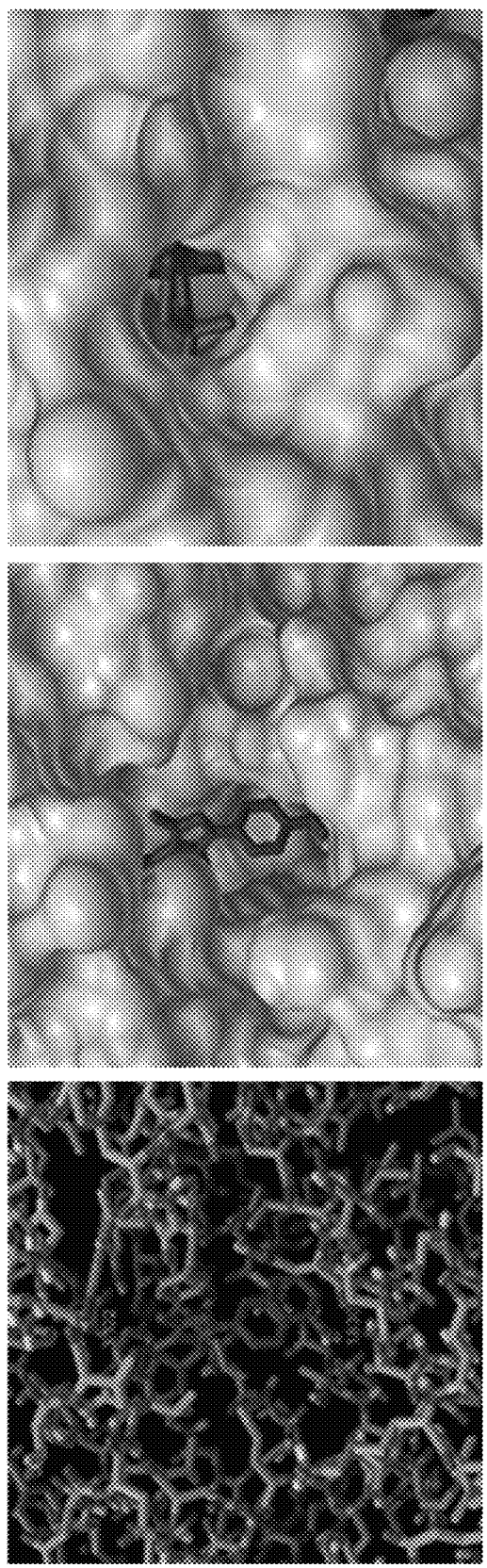

ANTIMICROBIAL COMPOSITIONS, METHODS OF USE, AND METHODS OF TREATMENT OF INFECTIONS

CROSS-REFERENCE TO RELATED APPLICATIONS

This application claims the benefit of and priority to U.S. Provisional Application Ser. No. 62/166,327, having the title "ANTIMICROBIAL COMPOSITIONS, METHODS OF USE, AND METHODS OF TREATMENT OF INFECTIONS," filed on May 26, 2015, the disclosure of which is incorporated herein in by reference in its entirety.

BACKGROUND

In spite of the rapid and continued emergence of drug resistant pathogens, there has been an alarming decline in drug discovery efforts in the pharmaceutical industry. Thus, there is a need to develop drugs to treat infections for pathogens.

SUMMARY

The present disclosure provides compositions including a compound (e.g., compounds A-D), pharmaceutical compositions including the compound and salts thereof, methods of treatment of a condition (e.g., an infection) or disease, methods of treatment using compositions or pharmaceutical compositions, and the like.

An exemplary embodiment of the present disclosure includes a pharmaceutical composition, among others, that includes: a therapeutically effective amount of a compound, or a pharmaceutically acceptable salt of the compound, and a pharmaceutically acceptable carrier, to treat an infection, wherein the compound has one of the following structures:

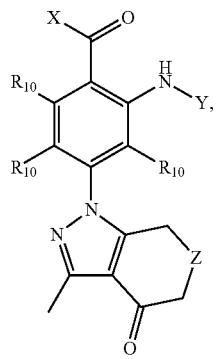

A

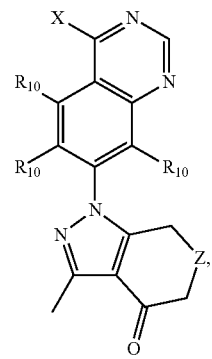

B

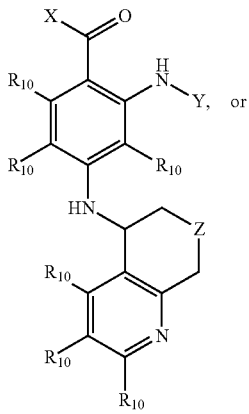

C

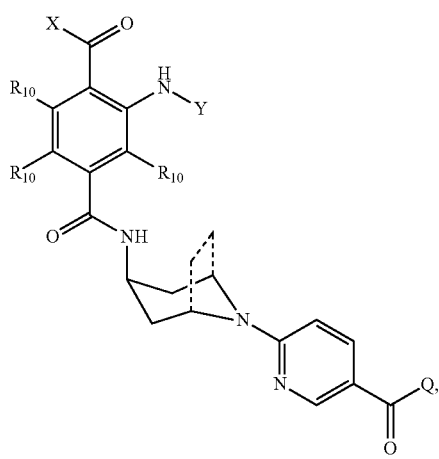

D wherein X is selected from the group consisting of: $NR_5R_6$, OH, and $-O-R_7$, wherein $R_5$, $R_6$, and $R_7$ are each independently selected from a group consisting of H, a substituted or unsubstituted, linear or branched aliphatic group (e.g., alkyl) is optionally partially or fully cyclized and where up to two of the carbons is optionally replaced by $OR_8$, $NH_2$, $NHR_8$, $NR_{8(2)}$, $NH-(C=O)R_8$, $(C=O)R_8$, or $S(O)_nR_8$, where n=0-2, wherein each $R_8$ is independently selected from a group consisting of H, a substituted or unsubstituted, linear or branched aliphatic group (e.g., alkyl) that is optionally partially or fully cyclized and where up to two of the carbons is optionally replaced by $OR_9$, $NH_2$, $NHR_9$, $NR_{9(2)}$, $NH-(C=O)R_9$, $(C=O)R_9$, or $S(O)_nR_9$, where n=0-2, wherein $R_9$ is independently selected from a group consisting of H, a substituted or unsubstituted, linear or branched aliphatic group (e.g., alkyl); wherein Y is selected from the group consisting of H, a substituted or unsubstituted, linear or branched aliphatic group (e.g., alkyl) is optionally partially or fully cyclized and where up to two of the carbons is optionally replaced by $OR_8$, $NH_2$, $NHR_8$, $NR_{8(2)}$, $NH-(C=O)R_8$, $(C=O)R_8$, or $S(O)_nR_8$, where n=0-2; wherein Z is selected from the group consisting of: $NR_1$, S, $PR_1R_2$, $SiR_1R_2$, and $CR_1R_2$, wherein if Z is C, then $R_1$ and $R_2$ are not methyl; wherein $R_1$ and $R_2$ are each independently selected from the group consisting of: selected from a group consisting of H, a substituted or unsubstituted, linear or branched aliphatic group (e.g., alkyl) is optionally partially or fully cyclized and where up to two of the carbons is optionally replaced by $OR_8$, $NH_2$, $NHR_8$, $NR_{8(2)}$, $NH-(C=O)R_8$, $(C=O)R_8$, or $S(O)_nR_8$, where n=0-2; wherein each $R_{10}$ are independently selected from the group consisting of: selected from a group consisting of H, a substituted or unsubstituted, linear or branched aliphatic group (e.g., alkyl) is optionally partially or fully cyclized and where up to two of the carbons is optionally replaced by $OR_8$, $NH_2$, $NHR_8$, $NR_{8(2)}$, NH—(C═O)$R_8$, (C═O)$R_8$, or S(O)$_n R_8$, where n=0-2; wherein Q is selected from the group consisting of: $NR_5R_6$, a substituted or unsubstituted, linear or branched aliphatic group (e.g., alkyl) is optionally partially or fully cyclized and where up to two of the carbons is optionally replaced by $OR_8$, $NH_2$, $NHR_8$, $NR_{8(2)}$, NH—(C═O)$R_8$, (C═O)$R_8$, or S(O)$_n R_8$, where n=0-2, and wherein the dashed bond in compound D is optionally present.

An exemplary embodiment of the present disclosure includes a method of treating an infection, among others, that includes: delivering to a subject in need thereof, a pharmaceutical composition, wherein the pharmaceutical composition includes a therapeutically effective amount of a compound, or a pharmaceutically acceptable salt of the compound, and a pharmaceutically acceptable carrier, to treat the infection, wherein the compound has a structure as described above (e.g., compounds A-D) or as otherwise described herein. In an embodiment, the infection can be caused by a microorganism, wherein the microorganism is selected from the group consisting of: *Leishmania, Enterococcus faecium, Staphylococcus aureus, Klebsiella pneumoniae, Acinetobacter baumannii, Pseudomonas aeruginosa,* and *Enterobacter cloacae*.

An exemplary embodiment of the present disclosure includes a composition, wherein the compound has a structure as described above (e.g., compounds A-D).

Other compositions, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure.

FIGS. 1A-1C illustrates docking studies of Compound 9c with human Hsp90 (Scheme 6, example 1). FIG. 1A represents the docked structure with all atoms visible, while 1B is the same pose using a space filling model. Rotation of 1B gives 1C, which shows a clear channel where one of the methyl groups points toward a cavity while the other points towards a hydrophobic pocket.

DISCUSSION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Prior to describing the various embodiments, the following definitions are provided and should be used unless otherwise indicated.

DEFINITIONS

Unless otherwise defined, all technical and scientific terms used herein have the same meaning as commonly understood by one of ordinary skill in the art of molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "substituted" refers to any one or more hydrogens on the designated atom that can be replaced with a selection from the indicated group, provided that the designated atom's normal valence is not exceeded, and that the substitution results in a stable compound. In an embodiment, one or more of the hydrogens can be substituted with a halogen, an alkyl group (unsubstituted or substituted), a cycloalkyl group (unsubstituted or substituted), an aryl group (unsubstituted or substituted), and the like. In particular, the term "substituted," as in "substituted alkyl", "substituted cycloalkyl," substituted aryl," or the like, means that the substituted group may contain in place of one or more hydrogens a group such as a halogen, an alkyl group (unsubstituted or substituted), a cycloalkyl group (unsubstituted or substituted), an aryl group (unsubstituted or substituted), and the like.

The term "aliphatic group" refers to a saturated or unsaturated, linear or branched hydrocarbon, substituted or unsubstituted, group and encompasses alkyl, alkenyl, and alkynyl groups, for example. Reference to an aliphatic group includes substituted and unsubstituted aliphatic groups.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms. Reference to an alkyl group includes substituted and unsubstituted alkyl groups.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like. Reference to an alkenyl group includes substituted and unsubstituted alkenyl groups.

The term "arylalkyl" refers to an arylalkyl group wherein the aryl and alkyl are as herein described. Examples of arylalkyl include, but are not limited to, -phenylmethyl, phenylethyl, -phenylpropyl, -phenylbutyl, and -phenylpentyl.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "carbocycles" refers to a monocyclic or multicyclic ring system of about 3 to about 14 carbon atoms, preferably of about 6 to about 10 carbon atoms. In an embodiment, carbocycle can refer to an aryl group. Exemplary carbocycles can refer to functional groups.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like. Reference to a cycloalkyl group includes substituted and unsubstituted cycloalkyl groups.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl. Reference to a cycloalkyl group includes substituted and unsubstituted cycloalkyl groups. Reference to a cycloalkenyl group includes substituted and unsubstituted cycloalkenyl groups.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted. Reference to an aryl group includes substituted and unsubstituted aryl groups.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, indazolyl, quinolyl, isoquinolyl, quinoxalyl, and quinazolinyl. Preferred examples are furanyl, indazolyl, imidazyl, pyranyl, pyrrolyl, and pyridyl. Reference to a heteroaryl group includes substituted and unsubstituted heteroaryl groups.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—$SCH_3$) and iso-propylsulfanyl (—$SCH(CH_3)_2$) and the like.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the subject.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the subject being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998).

The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing a composition of the present disclosure into a subject. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition (e.g., an infection), a disease or a disorder with a composition to affect the condition, disease or disorder by improving or altering it. The improvement or alteration may include an improvement in symptoms or an alteration in the physiologic pathways associated with the condition, disease, or disorder. "Treatment," as used herein, covers one or more treatments of an infection, a condition or a disease in a subject (e.g., a mammal, typically a human or non-human animal of veterinary interest), and includes: (a) reducing the risk of occurrence of the infection, condition, or a disease in a subject determined to be predisposed to the condition or disease but not yet diagnosed with it (b) impeding the development of the infection, and/or (c) relieving the infection, e.g., causing regression of the infection and/or relieving one or more infection symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition (e.g., infection), a disease, or a symptom thereof and/or may be therapeutic in terms of a partial or complete cure for an infection, and/or adverse effect attributable to the infection.

As used herein, the term "subject," or "patient," includes humans, mammals (e.g., mice, rats, pigs, cats, dogs, and horses), and birds. Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

Bacteria that cause bacterial infections are called pathogenic bacteria. The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium*, and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ra/stonia, Rhodococcus, Rickettsia Rochalimaea Roseomonas, Rothia, Ruminococcus, Salmonella, Selenomonas, Serpulina, Serratia, Shewenella, Shi-* gella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia, and Yokenella. Other examples of bacterium include Mycobacterium tuberculosis, M. bovis, M. typhimurium, M. bovis strain BCG, BCG substrains, M. avium, M. intracellulare, M. africanum, M. kansasii, M. marinum, M. ulcerans, M. avium subspecies paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, and other Nocardia species, Streptococcus viridans group, Peptococcus species, Peptostreptococcus species, Actinomyces israelii and other Actinomyces species, and Propionibacterium acnes, Clostridium tetani, Clostridium botulinum, other Clostridium species, Pseudomonas aeruginosa, other Pseudomonas species, Campylobacter species, Vibrio cholera, Ehrlichia species, Actinobacillus pleuropneumoniae, Pasteurella haemolytica, Pasteurella multocida, other Pasteurella species, Legionella pneumophila, other Legionella species, Salmonella typhi, other Salmonella species, Shigella species Brucella abortus, other Brucella species, Chlamydi trachomatis, Chlamydia psittaci, Coxiella bumetti, Escherichia coli, Neiserria meningitidis, Neiserria gonorrhea, Haemophilus influenzae, Haemophilus ducreyi, other Hemophilus species, Yersinia pestis, Yersinia enterolitica, other Yersinia species, Escherichia coli, E. hirae and other Escherichia species, as well as other Enterobacteria, Brucella abortus and other Brucella species, Burkholderia cepacia, Burkholderia pseudomallei, Francisella tularensis, Bacteroides fragilis, Fudobascterium nucleatum, Provetella species, and Cowdria ruminantium, or any strain or variant thereof. The Gram-positive bacteria may include, but is not limited to, Gram positive Cocci (e.g., Streptococcus, Staphyloccocus, and Enterococcus). The Gram-negative bacteria may include, but is not limited to, Gram negative rods (e.g., Bacteroidaceae, Enterobacteriaceae, Vibrionaceae, Pasteurellae and Pseudomonadaceae).

DISCUSSION

The present disclosure provides compositions including a compound (e.g., compounds A-D), pharmaceutical compositions including the compound, methods of treatment of a condition (e.g., an infection) or disease, methods of treatment using compositions or pharmaceutical compositions, and the like.

An embodiment of the present disclosure can be used individually or in combination (e.g., in the same composition or separately) with other antimicrobials to treat one or multiple types and/or strains of microorganisms such as bacteria, protozoa, and the like, which can include exposing the microorganisms to an appropriate amount of the composition to achieve the desired goal, by administering a therapeutically effective amount of the composition to the subject (e.g., human), or the like. Embodiments of the present disclose can be used as a broad spectrum antimicrobial (e.g., broad spectrum antibiotic, broad spectrum antiprotozoal, and the like). In an embodiment, compositions of the present disclosure can be used to treat subjects (e.g. humans) having infections caused by protozoa such as Leishmania, Plasmodium, and Toxoplasma, or a combination thereof by administering a therapeutically effective amount of the composition. In an embodiment, compositions of the present disclosure can be used to treat subjects having infections caused by bacteria such as: Enterococcus faecium, Staphylococcus aureus, Klebsiella pneumoniae, Acinetobacter baumannii, Pseudomonas aeruginosa, Enterobacter cloacae, or combinations thereof by administering a therapeutically effective amount of the composition. Additional details are described in the Examples.

An embodiment of the present disclosure includes a composition and a pharmaceutical composition including a compound such a compound A, B, C, or D or any of the other compounds described here. In an embodiment, the pharmaceutical composition and the method of treatment (e.g., of an infection such as one directly or indirectly caused by a microorganism infection) includes a therapeutically effective amount of a compound, or a pharmaceutically acceptable salt of the compound, and a pharmaceutically acceptable carrier, to treat the infection.

In an embodiment, the compound can include one of the following structures:

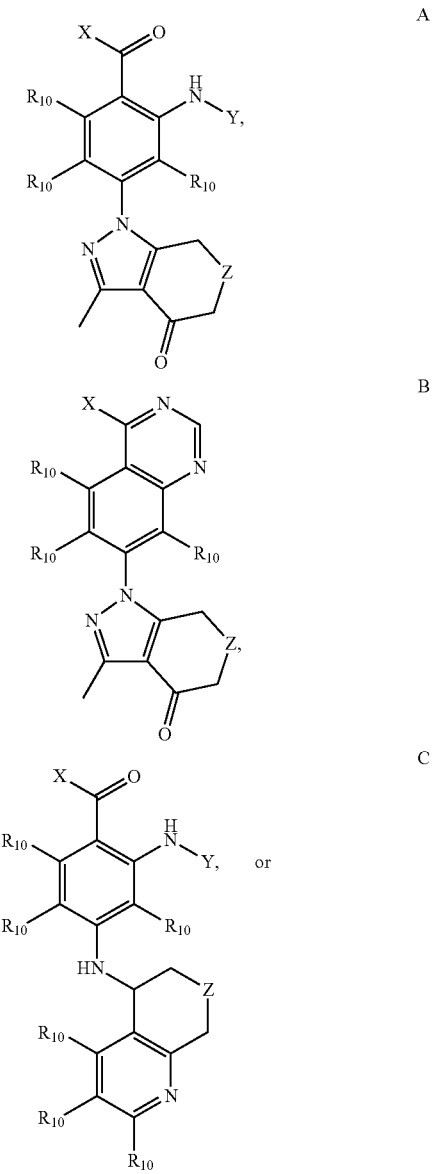

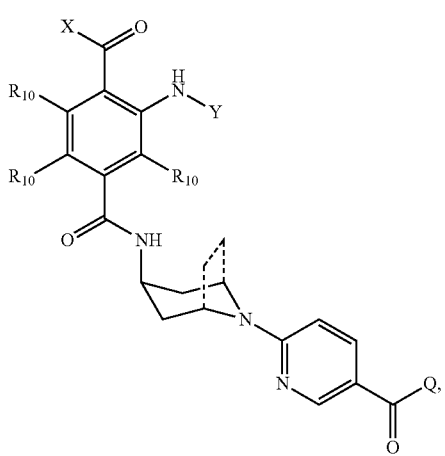

where the dashed bond in compound D is optionally present and can include 1 or 2 carbons.

In an embodiment, X can be selected from: $-NR_5R_6$, $-OH$, or $-O-R_7$. In an embodiment, $R_5$, $R_6$, and $R_7$ can each be independently selected from: H or a substituted or unsubstituted, linear or branched aliphatic group (e.g., an alkyl group (1 to 10 carbons)) that is optionally partially or fully cyclized and where up to two of the carbons is optionally replaced by $-OR_8$, $-NH_2$, $-NHR_8$, $-NR_{8(2)}$, $-NH-C(O)R_8$, $-C(O)R_8$, or $-S(O)_nR_8$, where n=0-2. In an embodiment, X can be $-NR_5R_6$, and $R_5$ and $R_6$ can each be independently selected from H or a substituted or unsubstituted, linear or branched alkyl group (e.g., methyl, ethyl, propyl, butyl). In an embodiment, X can be $-NH_2$.

In an embodiment, each $R_8$ can be independently selected from a group consisting of: H or a substituted or unsubstituted, linear or branched aliphatic group that is optionally partially or fully cyclized and where up to two of the carbons is optionally replaced by $-OR_9$, $-NH_2$, $-NHR_9$, $-NR_{9(2)}$, $-NH-C(O)R_9$, $-C(O)R_9$, or $-S(O)_nR_9$, where n=0-2. In an embodiment, $R_8$ can be H or an alkyl group (1 to 10 carbons).

In an embodiment, each $R_9$ can include: H or a substituted or unsubstituted, linear or branched aliphatic group. In an embodiment, each $R_9$ can each be independently selected from H or a substituted or unsubstituted, linear or branched alkyl group (e.g., methyl, ethyl, propyl, butyl). In an embodiment, $R_9$ can be H or an alkyl group (1 to 10 carbons).

In embodiments where $R_8$ or $R_9$ are within the carbon backbone (e.g., $-C-R_8-C-$) and not terminal atoms (e.g., terminal carbons, $-C-R_8$), the atoms (e.g., a carbon) will only have the number of bonds as permitted by the valence of the atom (e.g., carbon can have up to 4 bonds), and if to represent the structure correctly, a hydrogen must be removed or added, then the hydrogen is to be removed or added as one of skill would understand to conform to the proper valency.

In an embodiment, Y can be selected from: H or a substituted or unsubstituted, linear or branched aliphatic group (e.g., an alkyl group (1 to 10 carbons)) that is optionally partially or fully cyclized and where up to two of the carbons is optionally replaced by $-OR_8$, $-NH_2$, $-NHR_8$, $-NR_{8(2)}$, $-NH-C(O)R_8$, $-C(O)R_8$, or $-S(O)_nR_8$, where n=0-2. In an embodiment, Y can be selected from H or a substituted or unsubstituted, linear or branched alkyl group (e.g., methyl, ethyl, propyl, butyl), or an ether group (e.g., $C_{1\ to\ 10}-O-C_{1\ to\ 10}$, (e.g., $4CH_2)_i-O-CH_3$) ($-(CH_2)_2-O-CH_3$), $-(CH_2)_i-O-(CH_2)_j$-Ph ($-CH_2-O-CH_2$-Ph)), i=1, 2, 3, 4, 5, 6 and j=1, 2, 3, 4, 5, 6).

In an embodiment, Z can be selected from: $-NR_1$, $-S$, $-PR_1R_2$, $-SiR_1R_2$, or $-CR_1R_2$. In an embodiment, if Z is C, then $R_1$ and $R_2$ are not methyl. In an embodiment, $R_1$ and $R_2$ can each be independently selected from: H or a substituted or unsubstituted, linear or branched aliphatic group (e.g., an alkyl group (1 to 10 carbons)) that is optionally partially or fully cyclized and where up to two of the carbons is optionally replaced by $-OR_8$, $-NH_2$, $-NHR_8$, $-NR_{8(2)}$, $-NH-C(O)R_8$, $-C(O)R_8$, or $-S(O)_nR_8$, where n=0-2.

In an embodiment, each of $R_1$ and $R_2$ are independently selected from H; a substituted or unsubstituted, linear or branched alkyl group (e.g., methyl, ethyl, propyl, butyl); $-CH_2$-Ph; an ester group (e.g., $-C(O)R_{11}$, where $R_{11}$ can be an alkyl group (e.g., $-C(O)CH_uCH_3$ (u=1, 2, 3, 4) ($-C(O)CH_2CH_3$); $CH_2-O-CH_3$; -Ph; -(cyclo)$C_5H_{11}$); $-S(O_2)R_{12}$, where $R_{12}$ can be a substituted or unsubstituted, linear or branched alkyl group (e.g., methyl, ethyl, propyl, butyl); $-C(O)N(H)CH_2$-Ph; $-C(O)NH_2$; or an ether group (e.g., $C_{1\ to\ 10}-O-C_{1\ to\ 10}$, (e.g., $-(CH_2)_i-O-CH_3$) ($-(CH_2)_2-O-CH_3$), $-(CH_2)_i-O-(CH_2)_j$-Ph($-CH_2-O-CH_2$-Ph)), i=1, 2, 3, 4, 5, 6 and j=1, 2, 3, 4, 5, 6).

In an embodiment, $R_1$ and $R_2$ can from a ring with Z to form a 3, 4, 5, or 6 membered ring. In an embodiment, $R_1$ and $R_2$ are both $CH_3$. In an embodiment, $R_1$ and $R_2$ are H. In an embodiment, $R_1$ is $-CH_2$-Ph or H when Z is $NR_1$. In an embodiment, $R_1$ is H and $R_2$ is $-CH_2-O-CH_2$-Ph. In an embodiment, $R_1$ is H and $R_2$ is $-CH_2-O-CH_3$. In an embodiment, $R_1$ is $-C(O)-$ alkyl, $-C(O)$-aryl, or $-C(O)$-cycloalkyl, when Z is $NR_1$. In an embodiment, $R_1$ is $-S(O_2)$-alkyl, when Z is $NR_1$. In an embodiment, $R_1$ is $-C(O)N(H)CH_2Ph$. In an embodiment, $R_1$ is $-C(O)NH_2$ when Z is $NR_1$. In an embodiment, $R_1$ is $-CH_3$ and $R_2$ is $-CH_2OCH_2Ph$.

In an embodiment, Q can be selected from: $-NR_5R_6$, a substituted or unsubstituted, linear or branched aliphatic group (e.g., an alkyl group (1 to 10 carbons)) is that optionally partially or fully cyclized and where up to two of the carbons is optionally replaced by $-OR_8$, $-NH_2$, $-NHR_8$, $-NR_{8(2)}$, $-NH-C(O)R_8$, $-C(O)R_8$, or $-S(O)_nR_8$, where n=0-2. In an embodiment, each of $R_5$ and $R_6$ are independently selected from H; a substituted or unsubstituted, linear or branched alkyl group (e.g., methyl, ethyl, propyl, butyl); an aryl; $NH_2$; an ether group (e.g., $-O-$ alkyl); and $-N(H)CH_2Ph$.

In an embodiment, each $R_{10}$ can be individually selected from: H, a substituted or unsubstituted, linear or branched aliphatic group (e.g., an alkyl group (1 to 10 carbons)) is that optionally partially or fully cyclized and where up to two of the carbons is optionally replaced by $-OR_8$, $-NH_2$, $-NHR_8$, $-NR_{8(2)}$, $-NH-C(O)R_8$, $-C(O)R_8$, or $-S(O)_nR_8$, where n=0-2. In an embodiment, each $R_{10}$ can be individually selected from H or an alkyl group (e.g., methyl, ethyl, propyl, butyl).

Although every combination of X, Y, Z, $R_1$-$R_{12}$, and Q are not specifically represented herein, each combination is intended to be included herein and is only not included for sake of clarity.

In an embodiment where the aliphatic group is partially or fully cyclized, the cycle can be a 3 to 8 membered ring that is alicyclic, heteroalicyclic, aromatic, or heteroaromatic. In an embodiment where the aliphatic group is partially cyclized, part of the aliphatic group can include one or more a linear or branched hydrocarbon linker groups (e.g., alkyl group) bonded to the cycle (e.g., aralkyl and heteroaralkyl, —(CH$_2$)$_n$-aryl-(CH$_2$)$_n$—H or —CH$_3$, where in n can be 0 to 10, or the like).

In an embodiment, the compound can be one of the following structures:

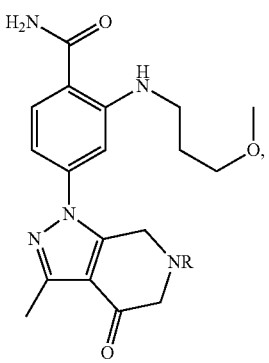

3

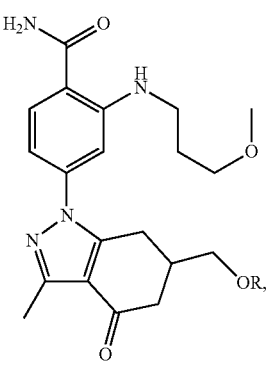

4

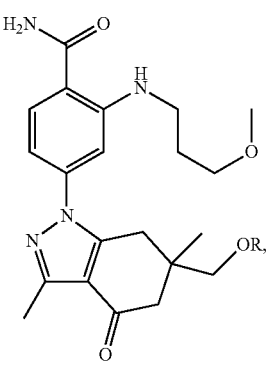

5

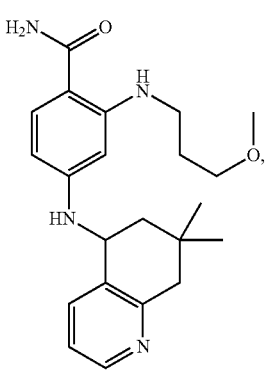

6

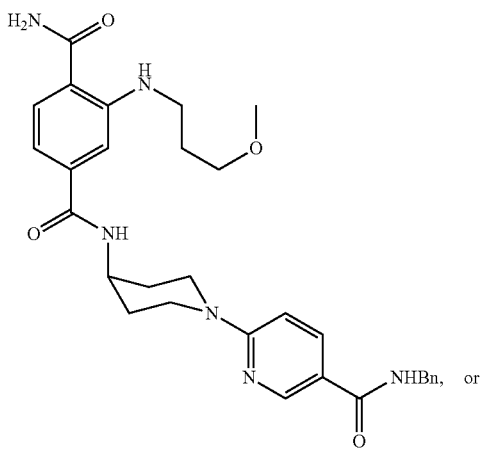

7

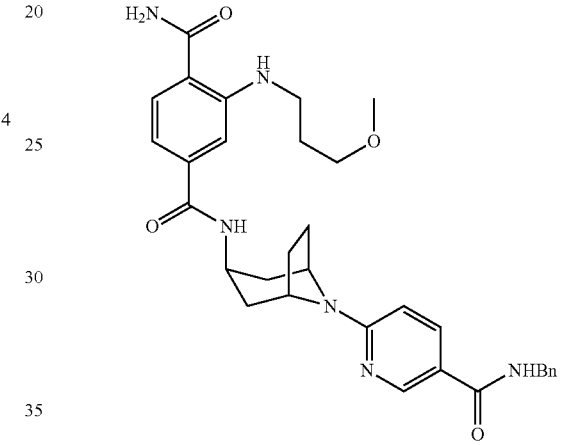

8 where R can be H, a substituted or unsubstituted, linear or branched aliphatic group (e.g., an alkyl group (1 to 10 carbons)) that is optionally partially or fully cyclized and where up to two of the carbons is optionally replaced by —OR$_8$, —NH$_2$, —NHR$_8$, —NR$_{8(2)}$, —NH—C(O)R$_8$, —C(O)R$_8$, or —S(O)$_n$R$_8$, where n=0-2.

In an embodiment, the method includes treating a subject having an infection, in particular, a bacterial infection or protozoal infection (e.g., leishmaniasis, malaria, and toxoplasmosis). The method can include delivering to a subject in need thereof, a pharmaceutical composition that includes a therapeutically effective amount of a compound (e.g., compounds A-D), or a pharmaceutically acceptable salt of the compound, and a pharmaceutically acceptable carrier, to treat the infection.

In an embodiment the infections can be caused by one or more types of bacteria, protozoa (e.g., *Leishmania*), and other microorganisms. In an embodiment the bacterial infections can be caused by for more types of bacteria (e.g., gram positive, gram negative, multiple families of bacteria, multiple types of bacteria, and the like)).

It should be noted that the therapeutically effective amount to result in uptake of the compound into the subject can depend upon a variety of factors, including for example, the age, body weight, general health, sex, and diet of the subject; the time of administration; the route of administration; the rate of excretion of the specific compound employed; the duration of the treatment; the existence of other drugs used in combination or coincidental with the specific composition employed; the type(s) of bacteria; and like factors well known in the medical arts.

Preparation of embodiments of the compounds is described in the Example.

Pharmaceutical Formulations and Routes of Administration

Embodiments of the present disclosure include a compound as identified herein and formulated with one or more pharmaceutically acceptable excipients, diluents, carriers and/or adjuvants. In addition, embodiments of the present disclosure include a compound formulated with one or more pharmaceutically acceptable auxiliary substances. In particular the compound can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the compound can be administered to the subject using any means capable of resulting in the desired effect. Thus, the compound can be incorporated into a variety of formulations for therapeutic administration. For example, the compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the compound may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the compound can be utilized in aerosol formulation to be administered via inhalation. Embodiments of the compound can be formulated into pressurized acceptable propellants such as dichlorodifluoromethane, propane, nitrogen and the like.

Furthermore, embodiments of the compound can be made into suppositories by mixing with a variety of bases such as emulsifying bases or water-soluble bases. Embodiments of the compound can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the compound in a composition as a solution in sterile water, normal saline or another pharmaceutically acceptable carrier.

Embodiments of the compound can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles in accordance with the present disclosure.

In an embodiment, the compound can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the compound can be accomplished using any of a variety of refillable, pump systems. Pumps provide consistent, controlled release over time. In some embodiments, the compound can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., compounds A-D) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the compound are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the compound may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the compound described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the compound can be administered to a subject in one or more doses. Those of skill will readily appreciate that dose levels can vary as a function of the specific the compound administered, the severity of the symptoms and the susceptibility of the subject to side effects. Preferred dosages for a given compound are readily determinable by those of skill in the art by a variety of means.

In an embodiment, multiple doses of the compound are administered. The frequency of administration of the compound can vary depending on any of a variety of factors, e.g., severity of the symptoms, and the like. For example, in an embodiment, the compound can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the compound is administered continuously.

The duration of administration of the compound analogue, e.g., the period of time over which the compound is administered, can vary, depending on any of a variety of factors, e.g., patient response, etc. For example, the compound in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the compound) to a subject (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the compound) can be administered in a single dose or in multiple doses.

Embodiments of the compound can be administered to a subject using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the compound. Where systemic delivery is desired, administration typically involves invasive or systemically absorbed topical or mucosal administration of pharmaceutical preparations.

In an embodiment, the compound can also be delivered to the subject by enteral administration. Enteral routes of administration include, but are not limited to, oral and rectal (e.g., using a suppository) delivery.

Methods of administration of the compound through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLE

Infectious diseases are among the greatest existing threats to human health. The World Health Organization has attributed nearly ⅓ of the burden of ill health in Africa to these afflictions, and yet there are insufficient methods available for their treatment. Furthermore, the organisms that cause these diseases continue to adapt to the current methods of treatment such that the threat of resistant infectious diseases is rapidly becoming a frightening reality. It is therefore imperative that new methods for the treatment of these diseases continue to be developed.

As part of an ongoing search for potential treatments for leishmaniasis, a screening campaign against available compounds was conducted using axenic amastigotes of *Leishmania donovani*, a protozoan that is known to cause visceral leishmaniasis (VL). Among the most active compounds found in this screening campaign was ketopyrazole 1, which had previously been reported as an inhibitor of heat shock protein 90 (Hsp90), a ubiquitous chaperone protein that has been explored as a therapeutic target for several indications including cancer and Alzheimer's disease. Given that this compound demonstrated activity in the axenic amastigote *L. donovani* assay, we felt that modified analogs could allow for the selective targeting of leishmaniasis, potentially through targeting the protozoan ortholog of Hsp90. Prior to taking on the development of novel analogs, we sought to synthesize an analog to confirm that the activity was readily reproducible. This was conducted as in Scheme 1, which gave analog 2, which proved to be equally active as 1 and thus prompted the discoveries outlined below. As a byproduct, compound 2a, which arose from the hydrolysis of the product amide to the corresponding carboxylic acid (not shown) was also isolated and evaluated (vide infra).

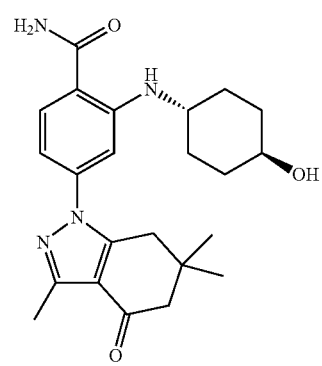

Scheme 1

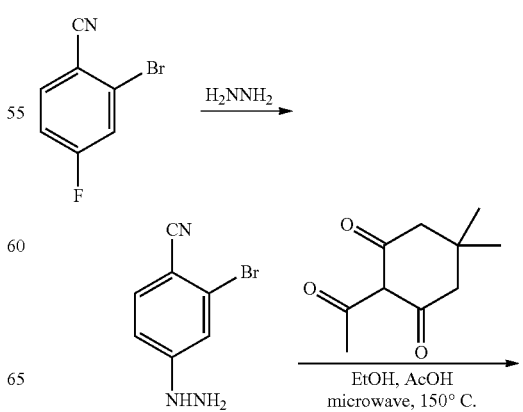

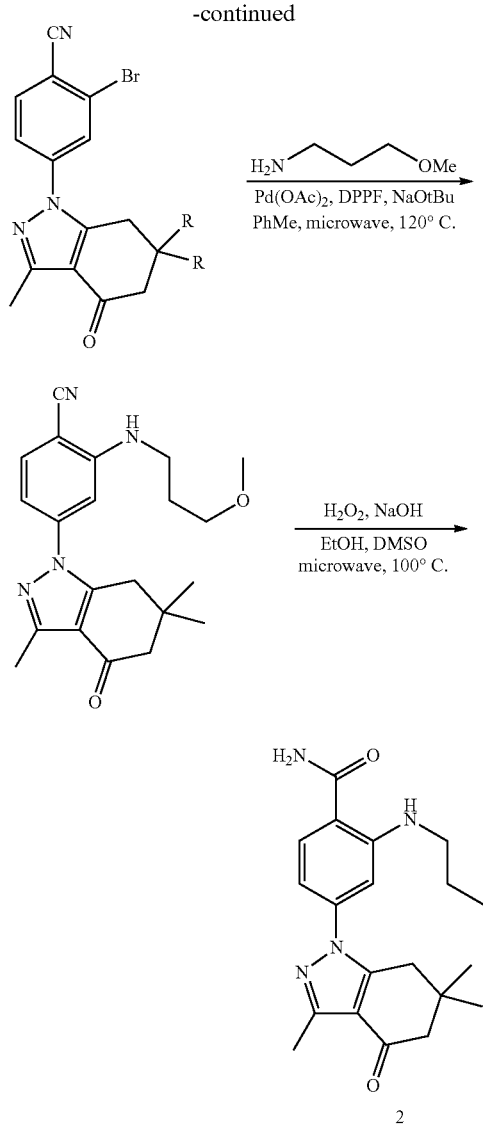

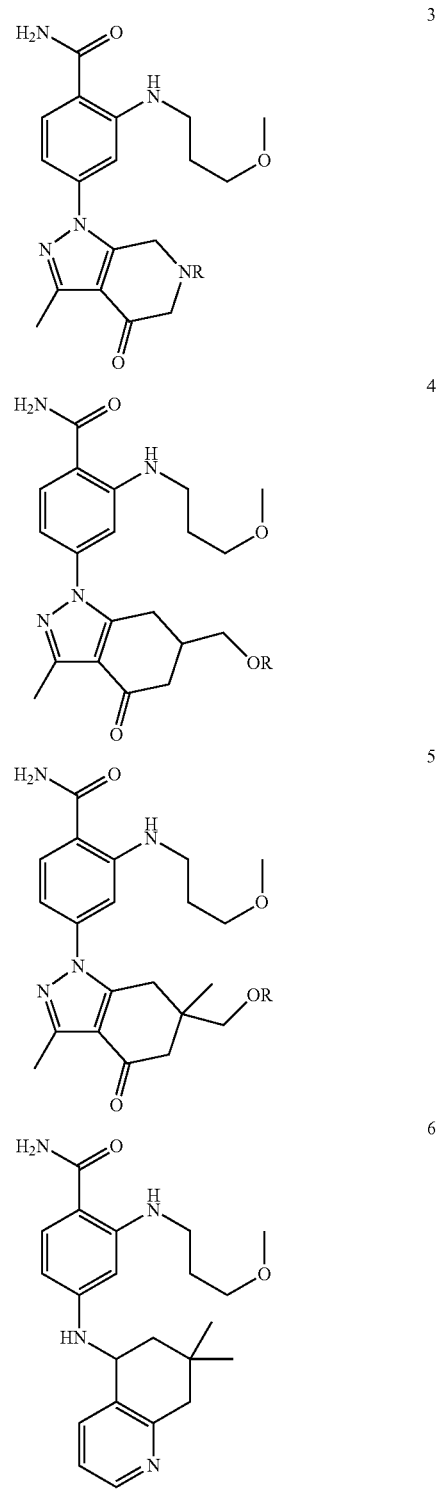

The initial discovery of these Hsp90 inhibitors also explored modifications to the amine (exemplified by the difference between analogs 1 and 2), but virtually ignored modifications to the bottom portion of the molecule as drawn. One of the only exceptions to this was the observation that removal of the geminal dimethyl groups led to a dramatic decrease in the activity against human Hsp90. We therefore reasoned that such a modification could lead to a series of compounds that would have a significant impact on their ability to interact with human Hsp90. What was unclear was whether this change would impact the antileishmanial activity due to changes between the human and protozoan orthologs. We therefore set out to synthesize a series of compounds that would ideally allow for the late-stage introduction of modifications at this position. Two such modifications are represented by 3 and 4 (R=H), which replace the geminal methyl groups with either a nitrogen (3) or an alcohol (4) that can be further modified into a series of analogs. We also synthesized 5 in order to retain the quaternary carbon at this position. Given that the interaction of 1 with Hsp90 is reported to proceed through an embedded hydrogen bond to the ketone moiety, we further designed analog 6 as a potential replacement for the initial core. Finally, given the presence of an anthranilamide in the initial hit compound and recognizing that it was also contained in other known Hsp90 inhibitors, we designed and synthesized analogs 7 and 8 as potential antileishmanial agents.

25
-continued
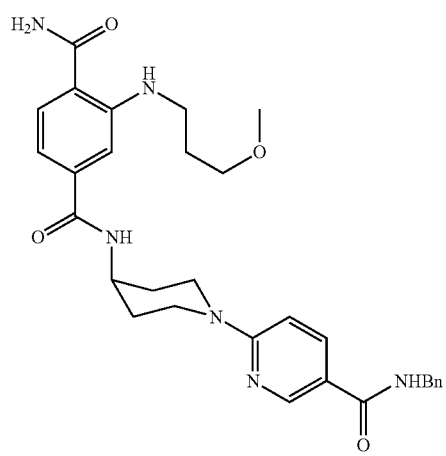
7
26
-continued
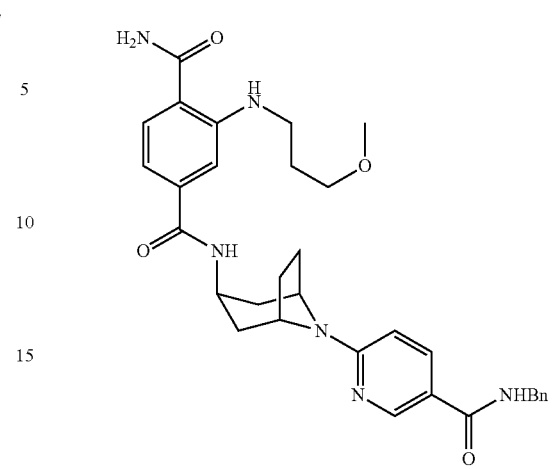
8
Scheme 2
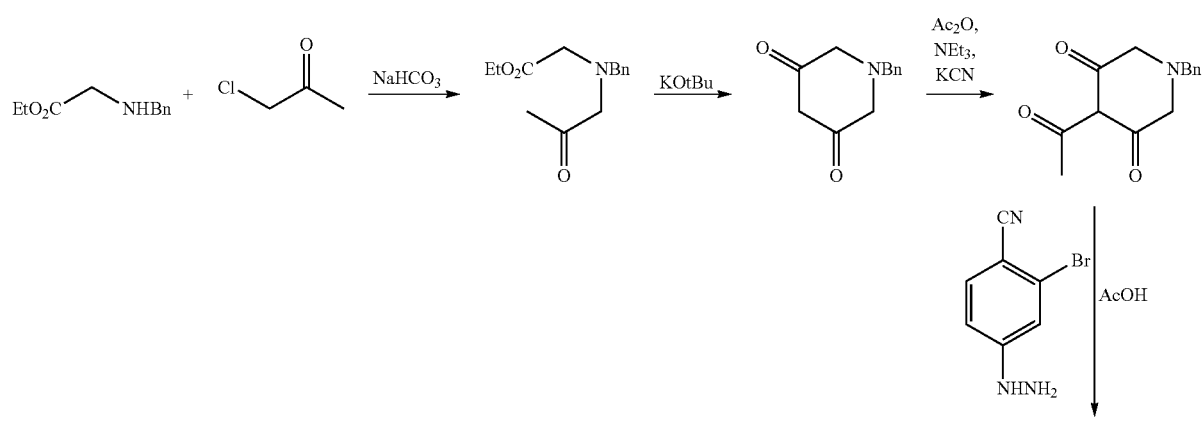
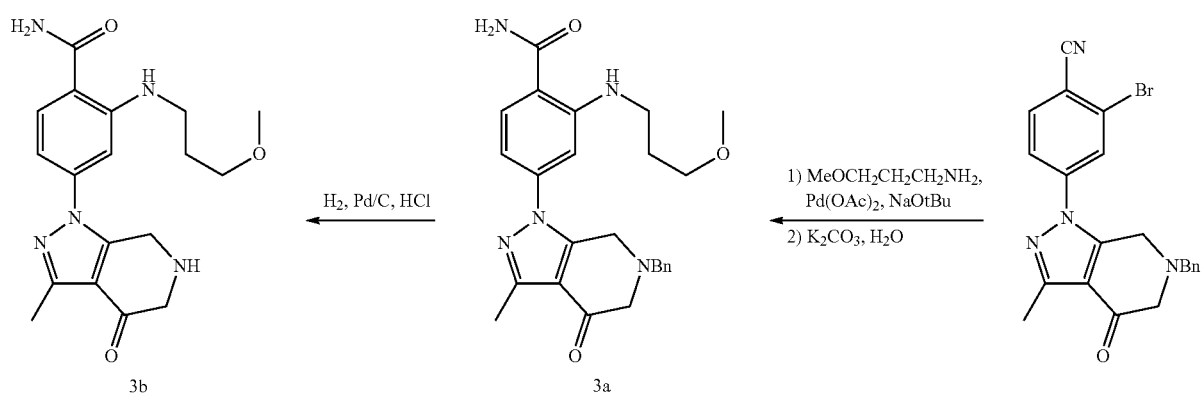

The synthesis of series 3 was conducted as in Scheme 2. Ethyl N-benzylglycinate was alkylated with chloroacetone, and the product was treated with potassium tert-butoxide to give the corresponding cyclic diketone. Acetylation of this material required the additional use of potassium cyanide, which served as an in situ transfer reagent to ensure that all of the acetylation occurred on the ring carbon rather than on oxygen. Condensation of this symmetrical triketone with the same aryl hydrazine used in Scheme 1 generated the tetrahydropyrazolo[3,4-c]pyridine ring system. Introduction of the amine sidechain under Buchwald-Hartwig conditions followed by hydration of the nitrile without oxidation gave 3a, which could be deprotected under acidic conditions to give secondary amine 3b. This deprotection also afforded a useful advanced intermediate that could be converted into several different types of analogs, which is illustrated in Scheme 3. Acylation with the appropriate acid chloride in pyridine was sufficient for the generation of a series of amides, which is illustrated by the synthesis of 3c-3h. Similarly, sulfonamides could be prepared via treatment with a sulfonyl chloride in the same solvent (3i). Ureas could be prepared through the reaction of 3b with the p-nitrocarbamate such as for the generation of 3j, which was selected because it could be debenzylated to provide primary urea 3k.

Series 4 was prepared as illustrated in Scheme 4. Birch reduction of 3,4,5-trimethoxybenzoic acid was followed by reduction of the carboxylate with lithium aluminum hydride to give the corresponding alcohol, which was subsequently alkylated with sodium hydride and benzyl bromide. The resulting diketone was acylated with acetic anhydride and Hunig's base to provide the requisite triketone, and cyclocondensation with the previously described hydrazine yielded the ketopyrazole. Installation of the amine sidechain and hydration of the nitrile proceeded as expected to give 4a, the first member of this series to be prepared. In a similar fashion, methyl analog 4b was prepared by the methylation of the alcohol obtained above and an identical series of steps. Using this methodology, a vast number of additional analogs of 4 could be prepared provided the appropriate alkyl halide (RX) could be obtained. It was initially our intention to utilize 4a as an advanced intermediate that could be debenzylated to provide the corresponding primary alcohol (R=H) that would allow subsequent derivatization in the final step, but we were unable to perform this chemical step without decomposition of the material, so these attempts were ultimately abandoned.

Scheme 3

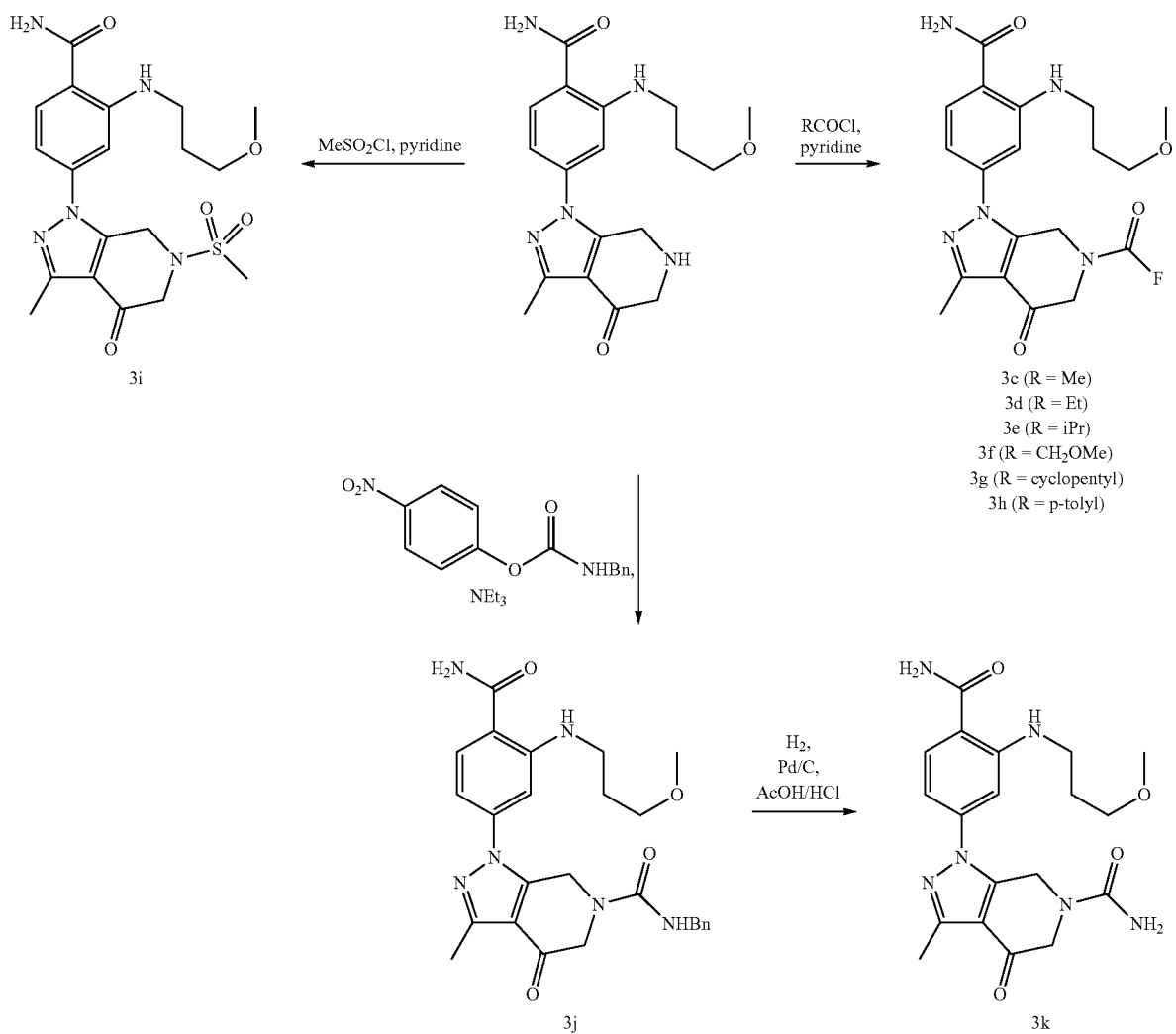

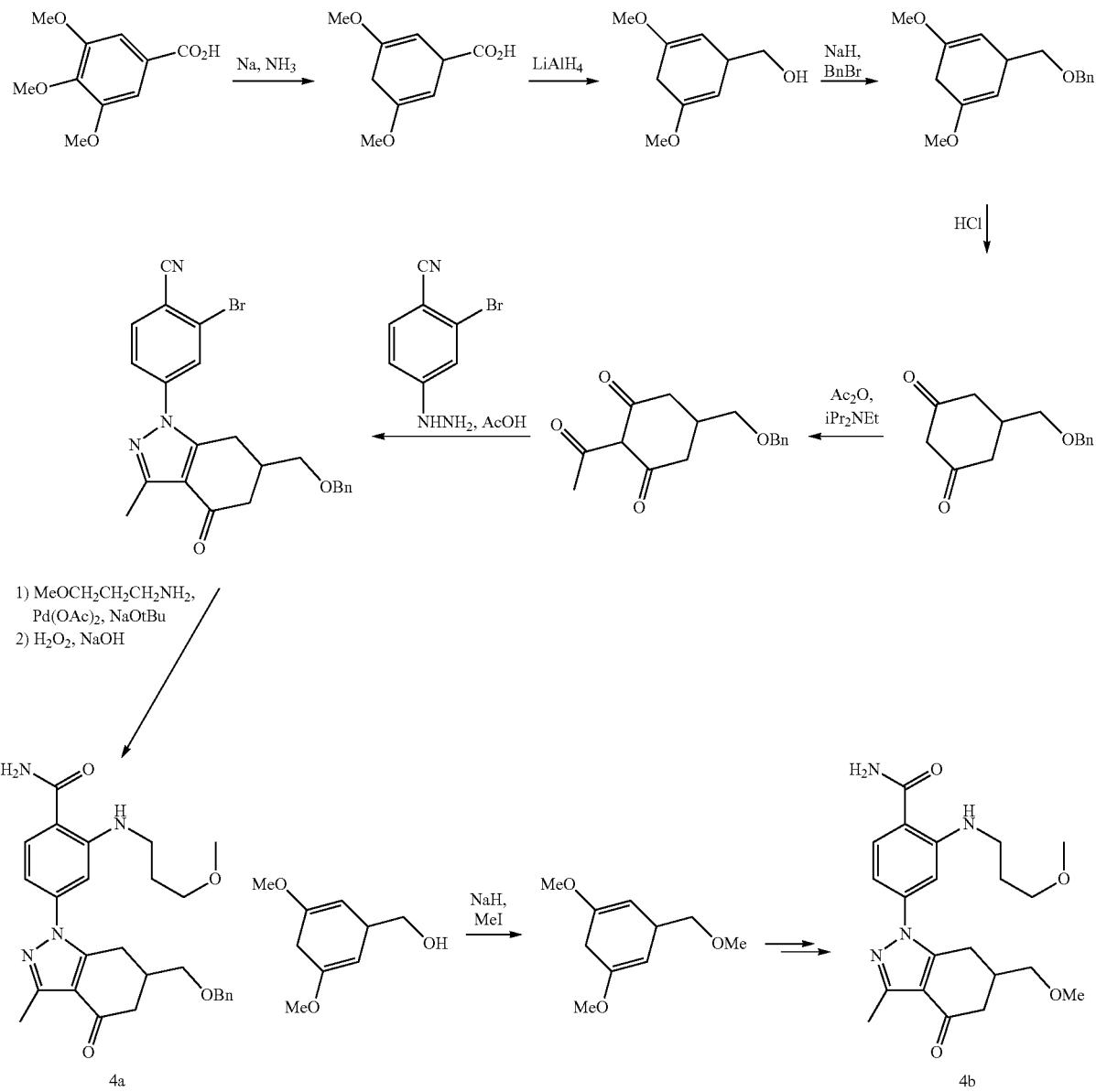

31

-continued

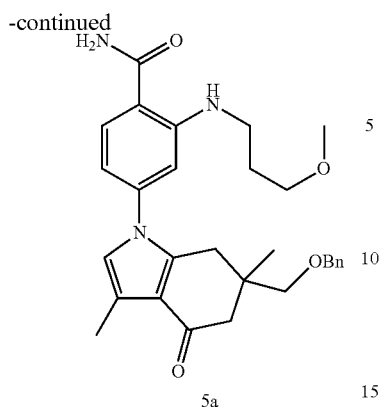

5a

Since the initial hits in our screening possess a quaternary carbon where the geminal methyl groups are positioned, we reasoned that a viable alternative scaffold would be to retain this quaternary nature, and the synthesis is detailed in Scheme 5. In our hands, it was better to conduct the tandem Birch reduction/alkylation on esterified materials, so 3,5-dimethoxybenzoic acid was first converted into the corresponding t-butyl ester, which was then reduced with potassium and worked up with methyl iodide to give the desired quaternary product. This ester was then reduced with lithium aluminum hydride and benzylated with sodium hydride and benzyl bromide, resulting in a reliable source of the protected neopentyl alcohol. Following the exact same steps outlined in Scheme 4, the quaternary scaffold was converted into 5a, which was the first member of this class of compounds and is currently being pursued as an alternative In an effort to identify an alternative series of compounds that would not require the amination/hydration sequence that has been demonstrated above, we prepared and analyzed quinazoline analogs as shown in Scheme 6. 4-Amino-7-fluoroquinazoline was directly substituted with hydrazine to give the cyclocondensation precursor, which could be converted directly into the corresponding ketopyrazoles under the same conditions we had previously optimized. In this fashion, we prepared ethers 9a and 9b, as well as the quaternary analog 9c.

In addition to these pyrazole-based derivatives, we sought to identify chemical entities that would orient hydrogen bond donating and accepting functionalities in a fashion similar to the compounds we had already prepared. We reasoned that tetrahydroquinoline compound 6 was a viable option, since the quinazoline nitrogen could mimic the ketone's ability to serve as a hydrogen bond acceptor. It was prepared as illustrated in Scheme 7. Condensation of 3-aminopropanol and dimedone followed by oxidative cyclization provided the tetrahydroquinoline ring, which was subjected to reductive amination with 4-amino-2-bromobenzonitrile. Finally, installation of the amine side chain and hydration of the nitrile gave 6.

Scheme 6

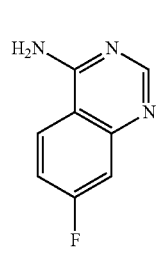

32

-continued

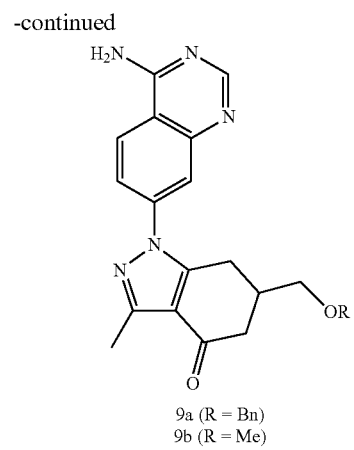

9a (R = Bn)
9b (R = Me)

9c (R = H)
9d (R = OBn)

Scheme 7

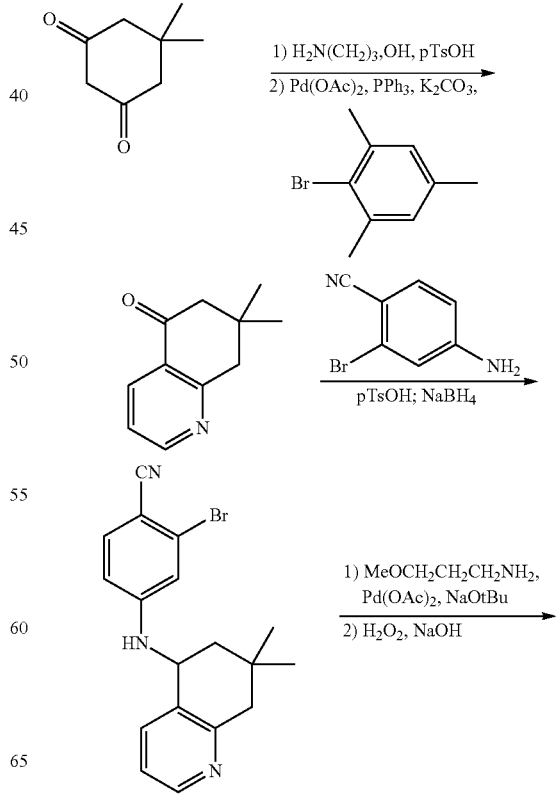

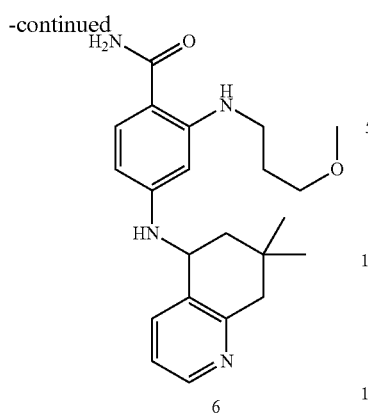

Since most of the analogs we had generated possessed a substituted anthranilamide motif, we recognized that other anthranilamides had previously been reported to show activity against Hsp90. We therefore set out to make analogs that merged the unique aspects of these scaffolds with the anthranilamide portion of our scaffold. Toward that end, we pursued the synthesis of compounds 7 and 8, which differ from each other only by the presence of an ethano bridge. Buchwald-Hartwig amination of ethyl 3-bromo-4-cyanobenzoate required more forcing conditions than we'd previously encountered, but was accomplished with the XANTPHOS ligand (Scheme 8). Conversion of the nitrile into the corresponding amide could be accomplished with concomitant saponification of the ethyl ester to give the requisite carboxylate coupling partner. It should be noted that a side product in this reaction was the corresponding dicarboxylic acid (a result of hydrolysis of the amide. This material was able to be used for the generation of additional analogs (vide infra).

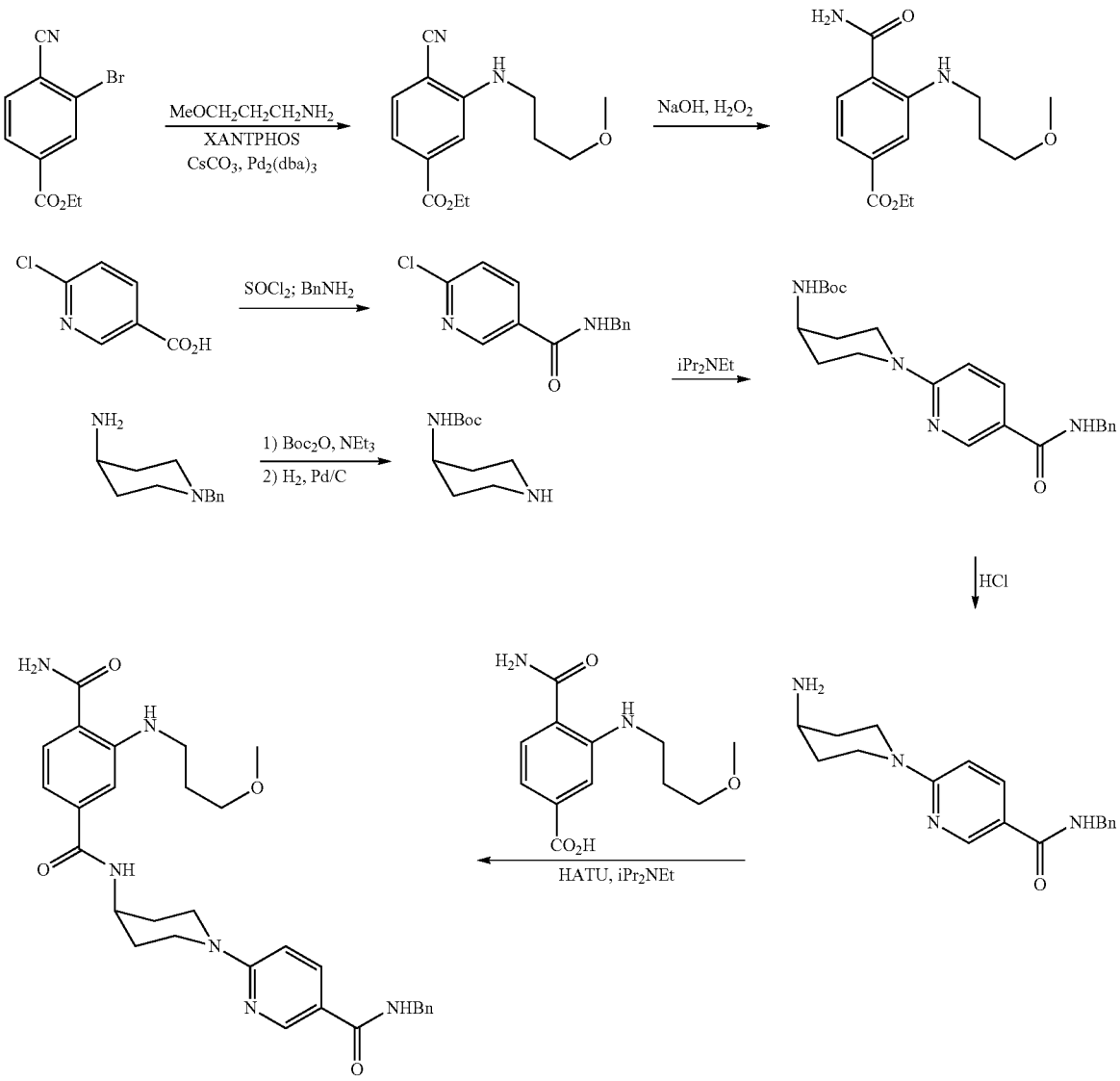

6-Chloronicotinic acid was activated as its acid chloride, then treated with benzylamine to generate the benzyl amide. This reaction could be achieved with other nucleophiles such as ammonia or ethanol to make the primary amide and ethyl ester analogs, respectively, and these analogs were also used to make additional derivatives (vide infra). Meanwhile, 4-amino-1-benzylpiperidine was protected as the tert-butyl-carbamate, which was then debenzylated with hydrogen and palladium on carbon to yield the free secondary amine. Arylation with the chloronicotinamide gave the desired coupled product, which was then deprotected with HCl and finally acylated with HATU and the carboxylic acid prepared above to afford 7.

The bridged analog 8 was synthesized as in Scheme 9. Reductive amination of commercially available Boc-nortropanone with benzyl amine occurred with good endo selectivity, and removal of the benzyl protecting group with Pearlman's catalyst led to the requisite primary amine. HATU coupling of this amine with the same carboxylic acid generated in Scheme 8 afforded the desired amide, which could be deprotected under acidic conditions and then arylated with a 6-chloronicotinamide derivative to provide the targeted product.

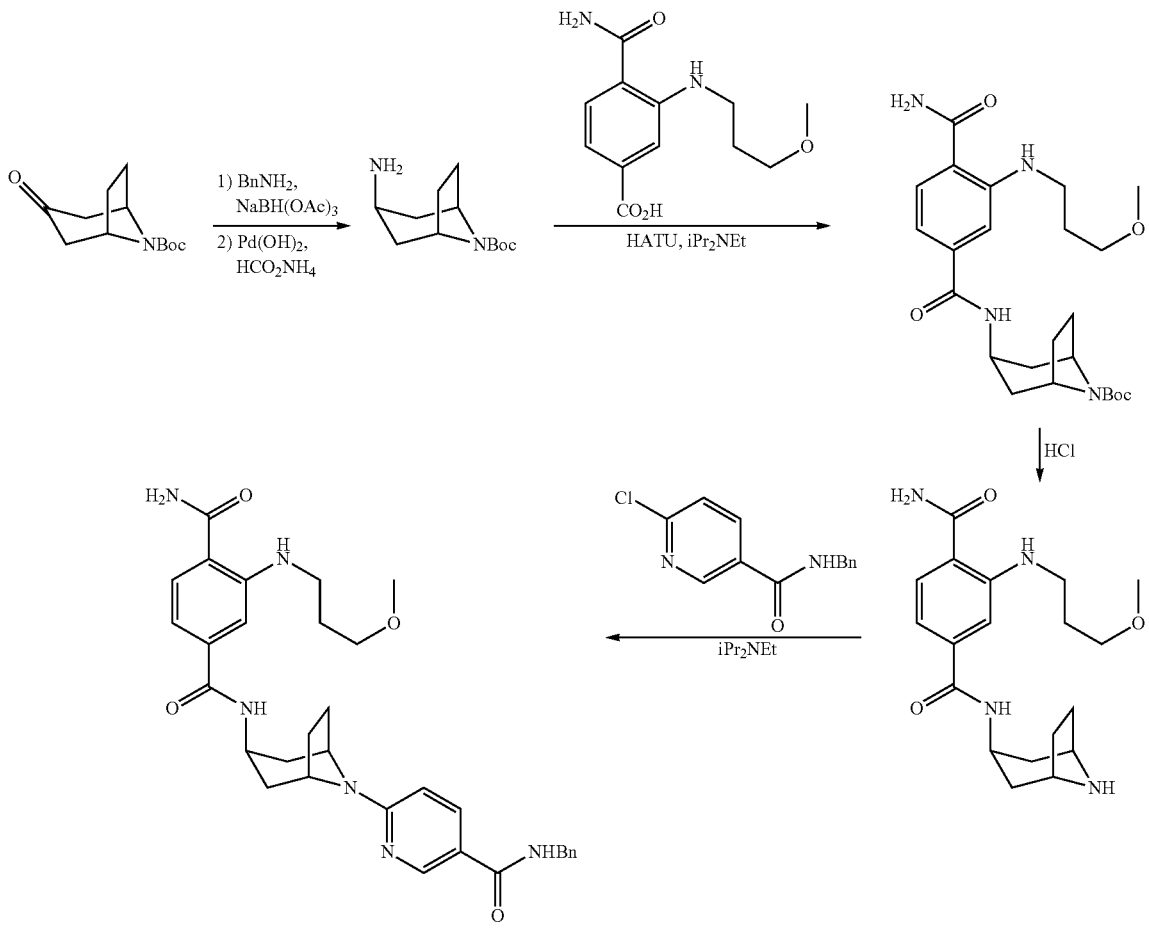

Scheme 9

In addition to the series prepared using the aforementioned schemes, a few additional one-off analogs were also prepared and are shown on the right. Since the hydration of the nitrile intermediate in Scheme 8 proceeded to give partial hydrolysis to the corresponding diacid, we prepared these acid analogs in order to evaluate the importance of the amide nitrogen (e.g. 7c-e, 8c-e). We also explored other nicotinamides (7a, 7b, 8a, 8b) in order to explore potential structure-activity relationships about this region of the molecule. Finally, we prepared methylated analog 9 in order to consider the ramifications of manipulating the planarity of the aryl substitution on the tetrahydro-pyrazole core. Each of these compounds was prepared using analogous methodology to that previously disclosed above.

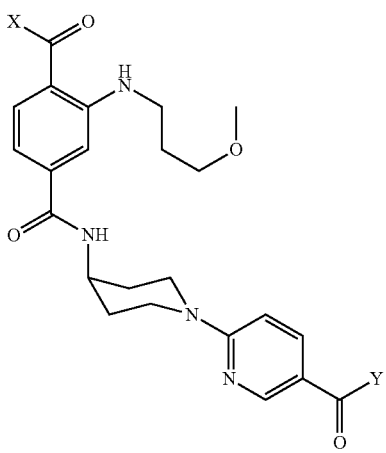

7a (X = Y = NH₂)
7b (X = NH₂, Y = OEt)
7c (X = OH, Y = NHBn)
7d (X = OH, Y = NH₂)
7e (X = OH, Y = OEt)

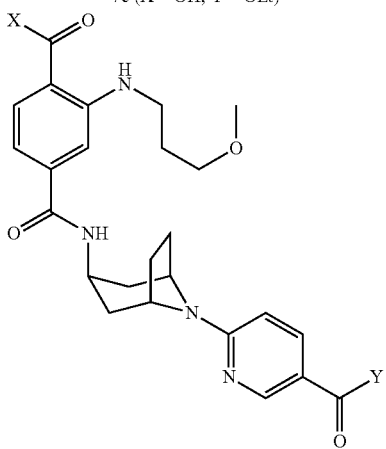

8a (X = Y = NH₂)
8b (X = NH₂, Y = OEt)
8c (X = OH, Y = NHBn)
8d (X = OH, Y = NH₂)
8e (X = OH, Y = OEt)

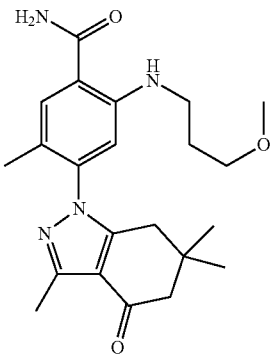

With a source of these compounds in hand, their activity against *Leishmania donovani* cells was evaluated in two different assays. *L. donovani* axenic amastigotes were generated from promastigotes and maintained in an appropriate medium such that their proliferation could be evaluated using a colorimetric assay. Additionally, macrophages were plated into a 96-well plate and a medium containing *L. donovani* was added and allowed to infect the macrophage cells. Subsequent addition of the compound to be evaluated was added to the wells prior to incubation and evaluation. Finally, a counterscreen for cytotoxicity was conducted using a J774 murine mouse cell line. Selected data for some of these compounds are provided below.

| | IC$_{50}$ (mg/mL) | | |
|---|---|---|---|
| Compound | Axenic Amastigote | Infected Macrophage | J774 Cytotoxicity |
| 2  | 0.646  | 0.879  | 3.521 |
| 2a | 5.185  | 0.8779 | 18.961 |
| 3a | 2.288  | 6.328  | >50 |
| 3b | 3.9    | >10    | >50 |
| 3c | 13.89  | 1.058  | >50 |
| 3d | 6.424  | 3.536  | >50 |
| 3e | 1.903  | 3.538  | 37.31 |
| 3f | 4.447  | 3.567  | >50 |
| 3g | 2.991  | 1.523  | >50 |
| 3h | 2.605  | 1.753  | 26.295 |
| 3i | >20    | >5.38  | 25.534 |
| 3j | >20    | >10    | >50 |
| 3k | >20    | >10    | >50 |
| 4a | >20    | TBD    | TBD |
| 4b | 6.442  | 1.769  | >50 |
| 5a | 10.196 | 0.613  | >1 |
| 6  | 2.551  | 5.375  | 6.746 |
| 7  | 8.194  | 2.618  | 24.19 |
| 7a | >20    | >10    | >50 |
| 7b | >20    | 0.642  | 5.1558 |
| 7c | TBD    | TBD    | TBD |
| 7d | TBD    | TBD    | TBD |
| 7e | TBD    | TBD    | TBD |
| 8  | 8.799  | 0.886  | 7.767 |
| 8a | 10.519 | 3.564  | 2.88 |
| 8b | 1.797  | 5.068  | >50 |
| 8c | >20    | >10    | >50 |
| 8d | TBD    | TBD    | TBD |
| 8e | TBD    | TBD    | TBD |
| 9a | 2.234  | 3.539  | >50 |
| 9b | 18.578 | >10    | 17.432 |
| 9c | 2.42   | 1.333  | >50 |
| 9d | 7.755  | >10    | 7.175 |
| 10 | 2.654  | 0.65   | 12.55 |

Based on the partial data that we have already obtained, it is clear that these compounds show compelling activity against both leishmaniasis assays, and that this data is not driven by cytotoxicity.

Syntheses

General Procedures.

Unless otherwise noted, all materials were obtained from commercial suppliers and used without further purification. All reactions with air- and/or moisture-sensitive compounds were performed under an argon atmosphere in a flame-dried or oven-dried reaction flask, and reagents were added via syringe or cannula. Dry THF was obtained via distillation from sodium benzophenone ketyl. Microwave reactions were carried out with an Anton Paar Monowave 300 instrument. Preparative chromatography was carried out using Sorbtech silica gel (60 Å porosity, 40-63 μm particle size) in fritted MPLC cartridges and eluted with Thomson Instrument SINGLE StEP pumps. Thin layer chromatography analyses were conducted with 200 μm precoated Sorbtech fluorescent TLC plates. Plates were visualized by UV light and by staining with a variety of stains such as acidic anisaldehyde, acidic vanillin, ceric ammonium nitrate or iodine vapor. LC/MS data was obtained using an Agilent 1100 HPLC/MSD system equipped with a diode array detector running a methanol/water gradient. High resolution mass spectral data were obtained using an Agilent 6540 QTOF mass spectrometer. Nuclear magnetic resonance spectrometry was run on a Varian Inova 500 MHz or a Varian Inova 400 MHz spectrometer, and chemical shifts are listed in ppm correlated to the solvent used as an internal standard.

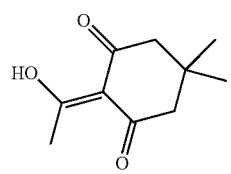

5

Triketone 5.

To a solution of dimedone (9.989 g, 71.3 mmol), Hunig's base (13.0 mL, 74.4 mmol) and DMAP (0.435 g, 3.56 mmol) in dichloromethane (200 mL) was added acetic anhydride (7.0 mL, 74 mmol), and the reaction was stirred at room temperature overnight. The solution was then concentrated on a rotary evaporator, and the resultant yellow oil that was partitioned between hexanes and 1 N HCl. The organic phase was then washed with saturated brine, dried over $MgSO_4$, filtered and concentrated on a rotary evaporator to give the product as a brown oil. Purification by flash chromatography (hexanes/ethyl acetate 9:1 to 2:1) gave 5 as a light yellow oil (11.6 g, 89%). $^1$H NMR (500 MHz, $CDCl_3$) δ 18.01 (s, 1H), 2.47-2.56 (m, 3H), 2.45 (s, 2H), 2.26 (s, 2H), 0.87-1.09 (m, 6H). $^{13}$C NMR (126 MHz, $CDCl_3$) δ 202.3, 197.8, 195.0, 112.3, 52.4, 46.8, 30.5, 28.4, 28.1. LRMS (ESI) m/z: $[M+H]^+$ 183.1.

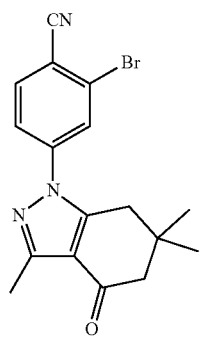

7

Pyrazole 7.

To a solution of 2-bromo-4-hydrazinylbenzonitrile (2.1560 g, 10.17 mmol) and 5 (1.8586 g, 10.20 mmol) in methanol (40 mL) was added acetic acid (1 mL), and the reaction was allowed to stir at room temperature for 72 h. During this time, the reaction turned cloudy and an orange precipitate formed. The mixture was concentrated on a rotary evaporator and purified by flash chromatography (hexanes/ethyl acetate 9:1 to 1:1) to give 7 as an orange solid (2.1546 g, 59%). $^1$H NMR (500 MHz, DMSO-$d_6$) δ 8.07-8.13 (m, 2H), 7.80 (dd, J=2.20, 8.56 Hz, 1H), 3.00 (s, 2H), 2.39 (s, 3H), 2.33 (s, 2H), 1.01 (s, 6H). $^{13}$C NMR (126 MHz, DMSO-$d_6$) δ 193.3, 151.0, 150.1, 142.9, 136.4, 127.1, 125.9, 122.6, 117.7, 117.3, 113.3, 52.1, 36.6, 35.9, 28.2, 13.6. LRMS (ESI) m/z: $[M+H]^+$ 357.8/359.8.

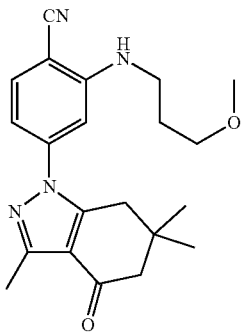

7.1

Nitrile 7.1.

A mixture of 7 (400.0 mg, 1.117 mmol), 1,1'-bis(diphenylphosphino)ferrocene (61.5 mg, 0.741 mmol), sodium 2-methylpropan-2-olate (215 mg, 2.23 mmol) and 3-methoxypropan-1-amine (199 mg, 2.23 mmol) in toluene (2 mL) was added to 30 mL microwave vial and heated to 120° C. for 20 min in a microwave reactor. Upon cooling, the mixture was taken up in dichloromethane, transferred to a round bottomed flask and concentrated on a rotary evaporator. The residue was purified by flash chromatography (hexanes/ethyl acetate 1:1) to give 7.1 as an off white solid (524 mg, 64%). $^1$H NMR (500 MHz, DMSO-$d_6$) δ 7.62 (d, J=8.31 Hz, 1H), 6.87 (s, 1H), 6.82 (d, J=8.31 Hz, 1H), 6.45-6.53 (m, 1H), 3.41 (t, J=5.62 Hz, 2H), 3.19-3.29 (m, 5H), 2.93 (s, 2H), 2.25-2.43 (m, 5H), 1.75-1.86 (m, 2H), 1.00 (s, 6H), 0.94-1.03 (m, 6H). $^{13}$C NMR (126 MHz, DMSO-$d_6$) δ 193.7, 151.7, 150.4, 149.2, 143.5, 135.1, 117.9, 117.1, 110.7, 105.4, 93.7, 70.4, 58.4, 52.1, 40.7, 36.9, 35.8, 28.6, 28.1, 13.5. LRMS (ESI) m/z: $[M+H]^+$ 367.2.

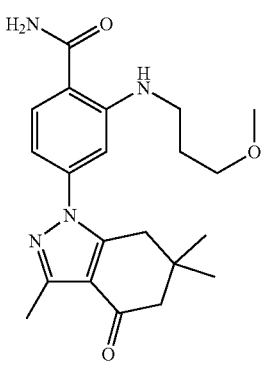

9

Amide 9.

A mixture of 7.1 (88 mg, 0.25 mmol), 50% sodium hydroxide (9.0 μL, 0.25 mmol) and 30% hydrogen peroxide (143 μL, 1.26 mmol) in ethanol (800 μL) and DMSO (200 μL) was added to a 2 mL microwave vial and heated to 100° C. for 40 min in a microwave reactor. Upon cooling, the mixture was transferred into a round bottom flask with ethyl acetate and concentrated on a rotary evaporator. The residue was purified via preparative HPLC using an acetonitrile/water gradient and lyophilized to give 9 as a white, fluffy solid (68 mg, 72%). $^1$H NMR (500 MHz, $CDCl_3$) δ 7.87-

8.31 (m, 2H), 7.47 (d, J=8.31 Hz, 1H), 6.80 (d, J=1.47 Hz, 1H), 6.62 (dd, J=1.47, 8.31 Hz, 1H), 3.50 (t, J=5.87 Hz, 2H), 3.26-3.36 (m, 5H), 2.81 (s, 2H), 2.53 (s, 3H), 2.38 (s, 2H), 1.93 (quin, J=6.36 Hz, 2H), 1.73-1.89 (m, 1H), 1.09 (s, 6H). $^{13}$C NMR (126 MHz, CDCl$_3$) δ 193.5, 171.3, 150.6, 150.0, 149.1, 142.7, 129.6, 117.2, 112.6, 109.5, 106.8, 70.2, 58.7, 52.4, 40.7, 37.6, 35.8, 29.1, 28.4, 13.4. HRMS m/z: [M+H]$^+$ Calcd for C$_{21}$H$_{29}$N$_4$O$_3$ 385.2240; Found 385.2248.

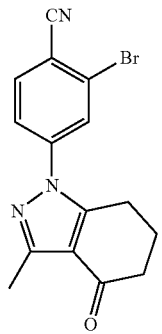

8

Pyrazole 8.

2-Acetyl-1,3-cyclohexanedione was treated under identical conditions to those described above for the synthesis of 7 to give 8 as an off-white solid (52%). $^1$H NMR (500 MHz, DMSO-d$_6$) δ 8.12 (br s, 1H), 8.12-8.08 (m, 1H), 7.80 (dd, J=8.50, 2.08 Hz, 1H), 3.07 (t, J=6.08 Hz, 2H), 2.44-2.36 (m, 2H), 2.39 (s, 3H), 2.05 (quin, J=6.21 Hz, 2H). $^{13}$C NMR (126 MHz, DMSO-d$_6$) δ 194.0, 152.2, 150.2, 143.0, 136.3, 127.0, 125.8, 122.6, 118.6, 117.3, 113.3, 38.2, 23.5, 23.4, 13.6. LRMS (ESI) m/z: [M+H]$^+$ 330.2/332.2.

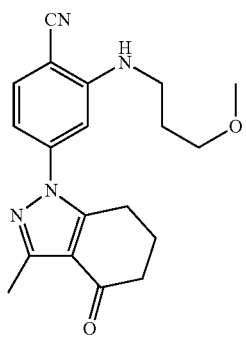

8.1

Nitrile 8.1.

Using conditions identical to those described above, 8 was converted into 8.1 as an off-white solid (74%). $^1$H NMR (500 MHz, CD$_3$OD) δ 7.54 (d, J=8.31 Hz, 1H), 6.92 (d, J=1.83 Hz, 1H), 6.82 (dd, J=8.31, 1.90 Hz, 1H), 3.54 (t, J=5.69 Hz, 2H), 3.38-3.33 (m, 2H), 3.35 (s, 3H), 3.04 (t, J=6.14 Hz, 2H), 2.52-2.50 (m, 2H), 2.46 (s, 2H), 2.22-2.09 (m, 2H), 2.02-1.84 (m, 2H). $^{13}$C NMR (126 MHz, CD$_3$OD) δ 195.4, 160.0, 151.6, 150.0, 143.2, 133.9, 117.6, 116.7, 110.4, 105.1, 94.3, 70.7, 57.6, 40.9, 37.6, 28.3, 23.4, 23.2, 12.0. LRMS (ESI) m/z: [M+H]$^+$ 339.4.

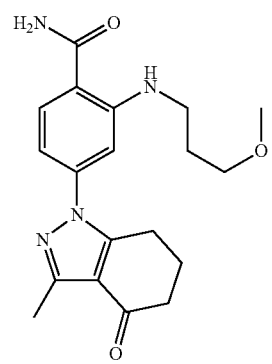

10

Amide 9.

Using conditions identical to those described above, 8.1 was converted into 10 as a fluffy white solid (81%). $^1$H NMR (500 MHz, DMSO-d$_6$) δ 8.40 (t, J=5.25 Hz, 1H), 7.90 (br s, 1H), 7.73 (d, J=8.44 Hz, 1H), 7.23 (br s, 1H), 6.77 (s, 1H), 6.69 (dd, J=8.42, 1.73 Hz, 1H), 3.40 (t, J=6.10 Hz, 2H), 3.22 (s, 3H), 3.18 (q, J=6.46 Hz, 2H), 3.01 (br t, J=5.93 Hz, 2H), 2.34-2.44 (m, 6H), 1.98-2.09 (m, 2H), 1.79 (quin, J=6.42 Hz, 2H). $^{13}$C NMR (126 MHz, CD$_3$OD) δ 195.5, 172.5, 151.4, 150.7, 149.7, 142.0, 130.0, 117.2, 113.4, 108.8, 105.7, 69.9, 57.5, 39.5, 37.7, 28.8, 23.4, 23.1, 12.0. HRMS m/z: [M+H]$^+$ Calcd for C$_{19}$H$_{26}$N$_4$O$_3$ 357.1927; Found 357.1926.

11

Quinazoline 11.

A solution of 7-hydrazinoquinazolin-4-ylamine (17.2 mg, 98 μmol) and 5 (26 mg, 0.14 mmol) in methanol (2 mL) was treated with acetic acid (1 μL) and stirred at room temperature for 3 d. The reaction was concentrated on a rotary evaporator to give a brown residue that was purified by preparative HPLC using an acetonitrile/water gradient. The combined purified fractions were lyophilized to give 11 as a light yellow solid (17.2 mg, 54%). $^1$H NMR (500 MHz, DMSO-d$_6$) δ 8.49 (s, 1H), 8.41-8.45 (m, 1H), 7.99 (br s, 2H), 7.79-7.83 (m, 2H), 3.09 (s, 2H), 2.49 (s, 3H), 2.41 (s, 2H), 1.09 (s, 6H). $^{13}$C NMR (126 MHz, CDCl$_3$) δ 193.5, 162.0, 157.0, 150.52, 150.47, 149.4, 142.0, 125.9, 121.1, 120.2, 117.2, 113.5, 52.2, 36.8, 35.9, 28.2, 13.6. HRMS m/z: [M+H]$^+$ Calcd for C$_{18}$H$_{20}$N$_5$O 322.1668; Found 322.1670.

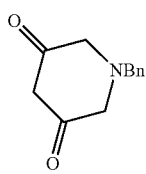

13

Piperidine 13.

A mixture of ethyl N-benzylglycinate (9.70 mL, 51.7 mmol) and sodium bicarbonate (4.79 g, 57.0 mmol) in THF (90 mL) and water (10 mL) was warmed to 60° C. in a round bottomed flask, and a solution of chloroacetone (4.26 mL, 51.7 mmol) in THF (20 mL) was added slowly. The warm reaction was then allowed to stir for an additional 18 h before it was cooled to room temperature, diluted with water (20 mL) and extracted with ethyl acetate. The combined organic extracts were washed with brine, dried over sodium sulfate and concentrated on a rotary evaporator to give a yellow oil. Purification by flash column chromatography (hexanes/ethyl acetate 1:1) gave the intermediate tertiary amine as a pale yellow oil (10.6 g, 82%). $^1$H NMR (500 MHz, CDCl$_3$) δ 7.21-7.39 (m, 5H), 4.14 (q, J=7.03 Hz, 2H), 3.82 (s, 2H), 3.51 (s, 2H), 3.44 (s, 2H), 2.10 (s, 3H), 1.34 (t, J=7.03 Hz, 3H). $^{13}$C NMR (126 MHz, CDCl$_3$) δ 207.8, 171.0, 138.1, 129.0, 128.4, 127.4, 63.1, 60.3, 58.4, 54.3, 27.5, 14.2. LRMS (ESI) m/z: [M+H]$^+$ 250.1.

A stirred solution of potassium tert-butoxide (6.62 g, 59.0 mmol) in t-butanol (60 mL) and ether (150 mL) was cooled to 0° C. under argon, and a solution of the intermediate tertiary amine (10.5 g, 42.1 mmol) in ether (50 mL) was added dropwise. The reaction was maintained at 0° C. for an additional 2 h, then allowed to warm to room temperature for 2 days. The resulting mixture was concentrated on a rotary evaporator, and the residue was triturated with ether (150 mL) and filtered. The precipitate was treated with a mixture of 10% aqueous acetic acid and stirred, and the precipitate that remained was collected by filtration and dried to give 13 (6.8 g, 79%) as an off-white solid which was used without further purification.

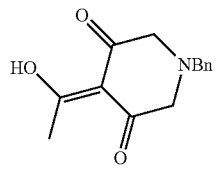

14

Triketone 14.

A solution of 13 (400 mg, 1.97 mmol) and triethylamine (410 μL, 2.94 mmol) in dichloromethane (50 mL) was stirred at room temperature under argon, and acetic anhydride (223 μL, 2.36 mmol) was added dropwise. The solution was stirred for an additional 20 min, then sodium cyanide (100 mg, 2.04 mmol) and potassium carbonate (1.00 g, 7.24 mmol) were added. The resulting mixture was warmed to 40° C. and stirred at that temperature for 36 h. The reaction was cooled to room temperature, filtered and diluted with water (50 mL). The resulting solution was extracted with dichloromethane, and the combined organic layers were dried over sodium sulfate and concentrated on a rotary evaporator to give a yellow oil. Purification by flash column chromatography (hexanes/ethyl acetate 2:1) gave 14 as a pale yellow oil (220 mg, 46%). $^1$H NMR (500 MHz, CDCl$_3$) δ 17.82 (br s, 1H), 7.29-7.38 (m, 5H), 3.69 (s, 2H), 3.36 (br s, 4H), 2.62 (s, 3H). $^{13}$C NMR (126 MHz, CDCl$_3$) δ 202.0 (×2), 129.2, 128.7 (×2), 128.0, 111.6, 61.2 (×2), 27.7. LRMS (ESI) m/z: [M+H]$^+$ 246.1.

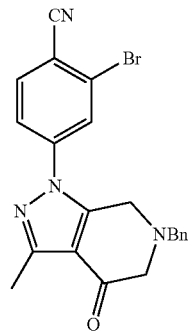

15

Pyrazole 15.

A mixture of 14 (800 mg, 3.26 mmol) in methanol (25 mL) containing a few drops of acetic acid was warmed to 40° C. until everything became homogeneous, then 2-bromo-4-hydrazinylbenzonitrile (761 mg, 3.59 mmol) was slowly added. Upon completion of the addition, the mixture was heated to 60° C. for 36 h. The solution was concentrated on a rotary evaporator to give a brown solid that was purified by flash column chromatography (hexanes/ethyl acetate 3:1) gave a yellow solid. Further recrystallization from methanol provided 15 as a yellow solid (750 mg, 55%). $^1$H NMR (400 MHz, CDCl$_3$) δ 7.86 (d, J=1.95 Hz, 1H), 7.68-7.75 (m, 1H), 7.43 (dd, J=1.95, 8.59 Hz, 1H), 7.25-7.33 (m, 5H), 3.95 (s, 2H), 3.78 (s, 2H), 3.31 (s, 2H), 2.52 (s, 3H). $^{13}$C NMR (101 MHz, CDCl$_3$) δ 190.4, 151.2, 148.4, 142.2, 136.2, 135.1, 128.9, 128.7, 127.9, 126.6, 126.5, 120.5, 118.0, 116.4, 114.5, 61.1 (×2), 49.6, 13.2. LRMS (ESI) m/z: [M+H]$^+$ 421.3/423.3.

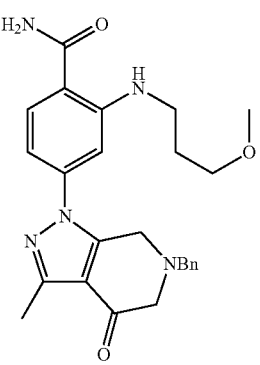

16

Tertiary Amine 16.

A mixture of 15 (4.00 g, 9.49 mmol), palladium acetate (1.10 g, 5.05 mmol), sodium tert-butoxide (1.00 g, 10.4 mmol) and 1,1'-ferrocenediyl-bis(diphenylphosphine) (788 mg, 9.49 mmol) in toluene (10 mL) in a 30 mL microwave vial was stirred at room temperature and 3-methoxypropan-1-amine (1.937 mL, 18.99 mmol) was added. The vial was then heated to 120° C. for 10 min in a microwave reactor, and the resulting mixture was cooled, filtered through Celite with dichloromethane (40 mL) and the filtrate was concentrated on a rotary evaporator to give a brown oil. Purification by flash column chromatography (hexanes/ethyl acetate 1:1) gave the intermediate nitrile as a yellow oil (2.50 g, 61%). $^1$H NMR (400 MHz, CDCl$_3$) δ 7.41 (d, J=8.20 Hz, 1H), 7.23-7.32 (m, 5H), 6.72 (d, J=1.95 Hz, 1H), 6.59 (dd, J=1.95, 8.20 Hz, 1H), 5.51 (t, J=4.88 Hz, 1H), 3.91 (s, 2H), 3.75 (s, 2H) 3.54 (t, J=5.47 Hz, 2H), 3.37 (s, 3H), 3.26-3.33 (m, 4H), 2.52 (s, 3H), 1.92 (quin, J=5.86 Hz, 2H). $^{13}$C NMR (101 MHz, CDCl$_3$) δ 190.6, 151.4, 150.2, 148.1, 143.1, 136.3, 133.9, 129.0, 128.6, 127.8, 117.3, 117.0, 109.6, 104.2, 95.0, 71.2, 61.3, 61.2, 58.8, 49.7, 42.0, 28.5, 13.2. LRMS (ESI) m/z: [M+H]$^+$ 430.2. The intermediate nitrile (400 mg, 0.931 mmol) was taken up in methanol (8 mL) and water (2 mL) in a 30 mL microwave vial, and potassium carbonate (142 mg, 1.024 mmol) was added. The mixture was then heated to 125° C. for 15 min in a microwave reactor, then cooled and diluted further with water (10 mL). The mixture was extracted with ethyl acetate, and the combined organic extracts were washed with brine, dried over sodium sulfate and concentrated on a rotary evaporator to give a yellow solid. Purification by flash column chromatography (hexanes/ethyl acetate 1:4) gave 16 as a yellow solid (140 mg, 34%). $^1$H NMR (500 MHz, CDCl$_3$) δ 8.08 (t, J=5.14 Hz, 1H), 7.43 (d, J=8.31 Hz, 1H), 7.13-7.32 (m, 5H), 6.67 (d, J=1.96 Hz, 1H), 6.53 (dd, J=2.20, 8.56 Hz, 1H), 6.06 (br s, 2H), 3.92 (s, 2H), 3.74 (s, 2H), 3.48 (t, J=5.87 Hz, 2H), 3.33 (s, 2H), 3.28 (s, 2H), 3.19-3.25 (m, 2H), 2.52 (s, 3H), 1.89 (quin, J=6.36 Hz, 2H). $^{13}$C NMR (101 MHz, CDCl$_3$) δ 190.8, 171.4, 151.1, 149.8, 148.1, 142.3, 136.4, 129.8, 129.0, 128.6, 127.8, 116.9, 112.3, 108.0, 105.0, 70.2, 61.3, 61.2, 58.7, 49.7, 40.1, 29.1, 13.3. HRMS m/z: [M+H]$^+$ Calcd for C$_{25}$H$_{30}$N$_5$O$_3$ 448.2349; Found 448.2322.

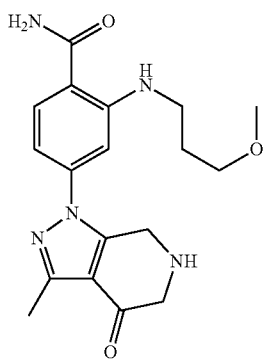

Secondary Amine 17.

A mixture of 16 (400 mg, 0.894 mmol) in 95% ethanol (25 mL) and 2N hydrochloric acid (447 µL, 0.894 mmol) was purged with argon in a 50 mL round bottomed flask and a catalytic amount of 10% palladium on carbon was added. The argon was evacuated under reduced pressure and the reaction was stirred under a balloon of hydrogen overnight. The mixture was filtered through Celite, washed with an additional aliquot of methanol and concentrated on a rotary evaporator to give a yellow solid. Purification by flash column chromatography (dichloromethane/methanol 19:1) gave 17 as a yellow solid (230 mg, 72%). $^1$H NMR (500 MHz, DMSO-d$_6$) δ 8.42 (t, J=5.38 Hz, 1H), 7.91 (br s, 1H), 7.74 (d, J=8.31 Hz, 1H), 7.24 (br s, 1H), 6.72 (d, J=1.96 Hz, 1H), 6.65 (dd, J=1.96, 8.31 Hz, 1H), 4.16 (s, 2H), 3.41 (t, J=6.11 Hz, 2H), 3.26 (s, 2H), 3.23 (s, 3H), 3.16-3.21 (m, 2H), 2.40 (s, 3H), 1.80 (quin, J=6.48 Hz, 2H). $^{13}$C NMR (126 MHz, DMSO-d$_6$) δ 194.4, 171.3, 151.3, 151.1, 148.8, 142.1, 130.9, 116.5, 113.2, 107.7, 104.4, 70.0, 58.4, 54.5, 42.9, 39.8, 29.1, 13.5. HRMS m/z: [M+H]$^+$ Calcd for C$_{18}$H$_{24}$N$_5$O$_3$ 358.1879; Found 358.1874.

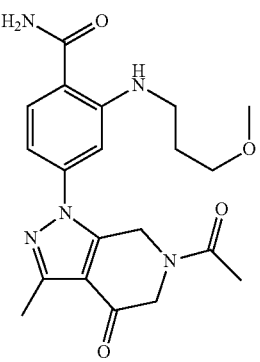

Acetamide 18.

To a stirred mixture of 17 (100 mg, 0.280 mmol) in pyridine (1 mL) was added acetic anhydride (26 µL, 0.280 mmol) dropwise. The resulting mixture was stirred at room temperature for an additional 1 h, then concentrated on a rotary evaporator to give a brown residue. Purification by flash column chromatography (dichloromethane/methanol 98:2) gave 18 as a tan solid (65 mg, 58%). $^1$H NMR (500 MHz, CDCl$_3$) δ 8.08 (br s, 1H), 7.48 (d, J=8.80 Hz, 1H), 6.66-6.80 (m, 1H), 6.52 (d, J=8.31 Hz, 1H), 6.25 (br s, 2H), 4.98 (s, 2H), 4.15 (s, 2H), 3.46 (t, J=5.87 Hz, 2H), 3.29 (s, 3H), 3.25 (q, J=6.03 Hz, 2H), 2.50 (s, 3H), 2.13 (s, 3H), 1.89 (quin, J=6.24 Hz, 2H). $^{13}$C NMR (126 MHz, CDCl$_3$) δ 187.0, 171.5, 169.9, 151.2, 150.2, 146.8, 141.9, 130.0, 116.5, 112.8, 107.9, 105.5, 70.2, 58.6, 54.5, 40.2, 39.2, 29.1, 21.7, 13.2. HRMS m/z: [M+H]$^+$ Calcd for C$_{20}$H$_{26}$N$_5$O$_4$ 400.1985; Found 400.1980.

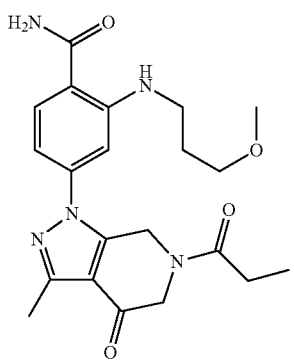

Propionamide 19.

Following a procedure identical to the one above using propionyl chloride, 19 was obtained as an off-white solid. $^1$H NMR (400 MHz, DMSO-d$_6$) δ 8.40 (d, J=5.08 Hz, 1H), 7.85-8.02 (m, 1H), 7.75 (d, J=8.20 Hz, 1H), 7.17-7.35 (m, 1H), 6.75 (br s, 1H), 6.65 (d, J=8.20 Hz, 1H), 5.01 (s, 2H), 4.20 (s, 2H), 3.38 (t, J=6.05 Hz, 2H), 3.20 (s, 3H), 3.12-3.19

(m, 2H), 2.39 (s, 3H), 2.32-2.38 (m, 2H), 1.73-1.83 (m, 2H), 0.91 (t, J=7.22 Hz, 3H). $^{13}$C NMR (126 MHz, DMSO-d$_6$) δ 188.4, 173.0, 171.2, 151.1, 149.2, 148.2, 141.6, 131.0, 116.4, 113.9, 107.9, 104.9, 70.0, 58.4, 53.8, 39.8, 39.3, 29.0, 26.2, 13.4, 9.6. HRMS m/z: [M+H]$^+$ Calcd for C$_{21}$H$_{28}$N$_5$O$_4$ 414.2141; Found 414.2136.

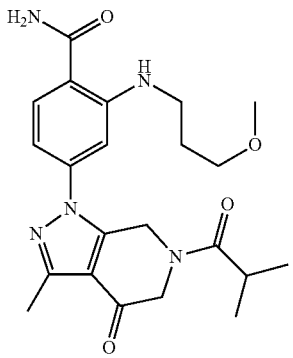

20

Isobutyramide 20.

Following a procedure identical to the one above using isobutyryl chloride, 20 was obtained as a tan solid. $^1$H NMR (500 MHz, CDCl$_3$) δ 8.12 (br s, 1H), 7.49 (d, J=8.31 Hz, 1H), 7.27 (s, 1H), 6.80 (br s, 1H), 6.61 (d, J=8.31 Hz, 1H), 5.88 (br s, 1H), 5.05 (br s, 1H), 4.24 (br s, 2H), 3.51 (t, J=5.87 Hz, 2H), 3.48 (s, 1H), 3.34 (s, 3H), 3.28-3.33 (m, 2H), 2.85 (m, 1H), 2.55 (s, 3H), 1.94 (quin, J=6.24 Hz, 2H), 1.79 (br s, 1H), 1.13 (d, J=6.36 Hz, 6H). $^{13}$C NMR (126 MHz, CDCl$_3$) δ 187.4, 176.3, 171.2, 151.3, 150.2, 147.2, 142.0, 129.8, 117.2, 112.6, 108.0, 105.6, 70.2, 58.6, 53.8, 40.2, 39.6, 30.6, 29.1, 19.2, 13.2. HRMS m/z: [M+H]$^+$ Calcd for C$_{22}$H$_{30}$N$_5$O$_4$ 428.2298; Found 428.2285.

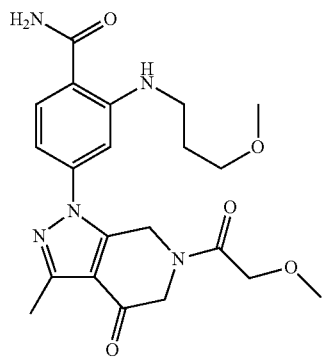

21

Methoxyacetamide 21.

Following a procedure identical to the one above using 2-methoxyacetyl chloride, 21 was obtained as an off-white solid. $^1$H NMR (500 MHz, DMSO-d$_6$) δ 8.32-8.55 (m, 1H), 7.95 (br s, 1H), 7.77 (d, J=8.80 Hz, 1H), 7.29 (br s, 1H), 6.78 (s, 1H), 6.68 (d, J=8.31 Hz, 1H), 5.02 (s, 2H), 4.17-4.27 (m, 2H), 4.16 (s, 2H), 3.41 (t, J=6.11 Hz, 2H), 3.11-3.26 (m, 8H), 2.41 (s, 3H), 1.81 (quin, J=6.36 Hz, 2H). $^{13}$C NMR (126 MHz, DMSO-d$_6$) δ 188.0, 171.2, 168.9, 151.1, 149.2, 147.7, 141.5, 131.0, 116.3, 113.9, 107.9, 104.9, 71.1, 70.0, 58.7, 58.4, 53.0, 39.8, 39.2, 29.0, 13.4. HRMS m/z: [M+H]$^+$ Calcd for C$_{21}$H$_{28}$N$_5$O$_5$ 430.2090; Found 430.2085.

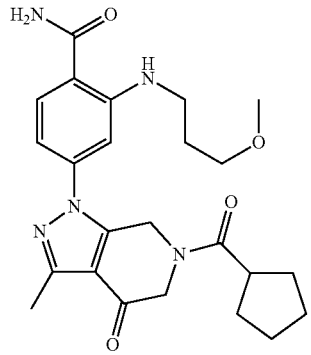

22

Cyclopentanecarboxamide 22.

Following a procedure identical to the one above using cyclopentanecarbonyl chloride, 22 was obtained as an off-white solid. $^1$H NMR (400 MHz, CD$_3$OD) δ 7.71 (d, J=8.20 Hz, 1H), 6.83 (s, 1H), 6.59-6.76 (m, 1H), 5.02-5.16 (s, 2H), 4.33 (s, 2H), 3.50 (t, J=5.86 Hz, 2H), 3.31 (s, 3H), 3.28 (td, J=1.56, 3.12 Hz, 2H), 3.00-3.13 (m, 1H), 2.47 (s, 3H), 1.89 (quin, J=6.44 Hz, 2H), 1.55-1.85 (m, 8H). $^{13}$C NMR (126 MHz, CD$_3$OD) δ 188.3, 176.2, 172.3, 150.9, 149.8, 147.9, 141.6, 130.3, 116.1, 113.6, 107.9, 104.9, 69.9, 57.5, 53.6, 40.9, 39.6, 39.4, 29.6, 28.7, 25.6, 11.8. HRMS m/z: [M+H]$^+$ Calcd for O$_{24}$H$_{32}$N$_5$O$_4$ 454.2454; Found 454.2440.

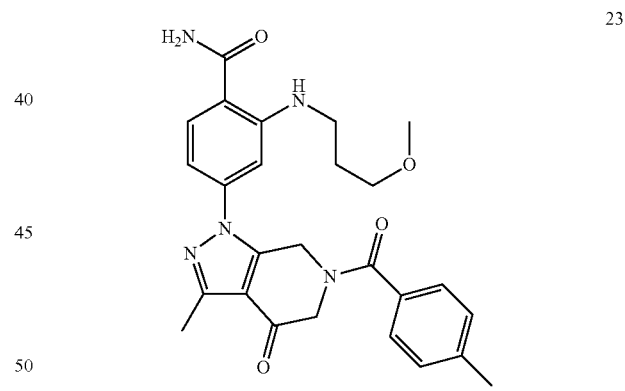

23 p-Tolylamide 23.

Following a procedure identical to the one above using 4-methylbenzoyl chloride, 23 was obtained as an off-white solid. $^1$H NMR (500 MHz, CDCl$_3$) δ 7.51 (d, J=7.83 Hz, 1H), 7.28-7.32 (m, 2H), 7.21-7.26 (m, 2H), 6.84 (br s, 1H), 6.66 (d, J=6.36 Hz, 1H), 5.60-5.95 (m, 2H), 5.17 (br s, 2H), 4.23 (br s, 2H), 3.53 (t, J=5.87 Hz, 2H), 3.36 (s, 3H), 3.33 (d, J=5.38 Hz, 2H), 2.57 (s, 3H), 2.39 (s, 3H), 1.96 (td, J=5.93, 12.11 Hz, 2H). $^{13}$C NMR (126 MHz, CDCl$_3$) δ 187.4, 171.6, 171.3, 151.2, 150.3, 143.7, 141.9, 141.1, 131.0, 130.1, 129.4, 129.1, 127.4, 116.8, 112.8, 107.9, 105.4, 70.2, 58.6, 50.5, 40.2, 29.1, 21.4, 13.2. HRMS m/z: [M+H]$^+$ Calcd for C$_{26}$H$_{30}$N$_5$O$_4$ 476.2298; Found 476.2293.

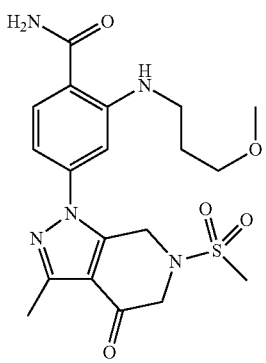

24

Sulfonamide 24.

To a stirred mixture of 17 (100 mg, 0.280 mmol) in pyridine (1.5 mL) was added methanesulfonyl chloride (24 µL, 0.31 mmol) dropwise. The resulting mixture was stirred at room temperature for an additional 1 h, then concentrated on a rotary evaporator to give a brown residue. Purification by flash column chromatography (dichloromethane/methanol 19:1) gave 24 as a tan solid (70 mg, 57%). $^1$H NMR (500 MHz, DMSO-$d_6$) δ 8.41 (br s, 1H), 7.95 (br s, 1H), 7.76 (d, J=8.31 Hz, 1H), 7.29 (br s, 1H), 6.76 (d, J=1.96 Hz, 1H), 6.64 (dd, J=1.96, 8.31 Hz, 1H), 4.82 (s, 2H), 3.99 (s, 2H), 3.41 (t, J=5.87 Hz, 2H), 3.22 (s, 3H), 3.17-3.21 (m, 2H), 3.03 (s, 3H), 2.43 (s, 3H), 1.80 (quin, J=6.48 Hz, 2H). $^{13}$C NMR (126 MHz, DMSO-$d_6$) δ 187.8, 171.2, 151.1, 149.3, 146.9, 141.4, 131.0, 116.2, 114.0, 107.9, 105.0, 70.0, 58.4, 53.3, 48.8, 39.8, 37.6, 29.0, 13.4. HRMS m/z: [M+H]$^+$ Calcd for $C_{19}H_{26}N_5O_5S$ 436.1655; Found 436.1664.

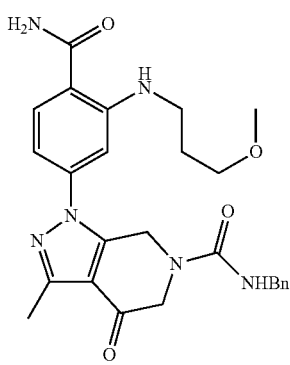

25

Benzyl Urea 25.

A solution of 17 (250 mg, 0.699 mmol), 4-nitrophenyl-N-benzylcarbamate (209 mg, 0.769 mmol) and triethylamine (107 µL, 0.769 mmol) in dichloromethane (20 mL) was stirred at room temperature overnight. The mixture was then diluted with dichloromethane (100 mL) and washed with water and brine. The resulting organic solution was dried over sodium sulfate and concentrated on a rotary evaporator to give an off-white residue. Purification by flash column chromatography (dichloromethane/methanol 19:1) gave 25 as an off-white solid (120 mg, 35%). $^1$H NMR (500 MHz, DMSO-$d_6$) δ 8.44 (t, J=5.38 Hz, 1H), 7.89-8.02 (m, 1H), 7.77 (d, J=8.31 Hz, 1H), 7.56 (t, J=5.87 Hz, 1H), 7.09-7.32 (m, 5H), 6.75 (d, J=1.96 Hz, 1H), 6.68 (dd, J=1.96, 8.31 Hz, 1H), 4.97 (s, 2H), 4.18 (d, J=5.38 Hz, 2H), 4.14 (s, 2H), 3.41 (t, J=6.11 Hz, 2H), 3.22 (s, 3H), 3.17-3.21 (m, 2H), 2.41 (s, 3H), 1.77-1.84 (m, 2H). $^{13}$C NMR (126 MHz, DMSO-$d_6$) δ 189.9, 171.2, 158.1, 151.1, 149.0, 148.8, 141.7, 140.8, 131.0, 128.5, 127.3, 127.0, 116.5, 113.6, 108.0, 104.9, 70.0, 58.4, 53.3, 44.0, 42.3, 39.8, 29.0, 13.4. HRMS m/z: [M+H]$^+$ Calcd for $C_{26}H_{31}N_6O_4$ 491.2407; Found 491.2410.

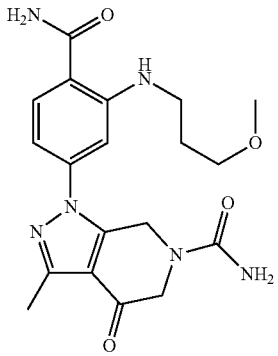

26

Urea 26.

A mixture of 25 (90 mg, 0.18 mmol) in acetic acid (5 mL) was purged with argon in a 50 mL round bottomed flask and a catalytic amount of 10% palladium on carbon was added. The argon was evacuated under reduced pressure and the reaction was stirred under a balloon of hydrogen overnight. The mixture was filtered through Celite, washed with an additional aliquot of methanol and concentrated on a rotary evaporator to give a brown solid. Purification by flash column chromatography (dichloromethane/methanol 19:1) gave 26 as a yellow solid (25 mg, 34%). $^1$H NMR (400 MHz, DMSO-$d_6$) δ 8.41 (br s, 1H), 7.93 (br s, 1H), 7.76 (d, J=8.40 Hz, 1H), 7.26 (br s, 1H), 6.74 (s, 1H), 6.66 (d, J=8.30 Hz, 1H), 6.37 (br s, 2H), 4.88 (s, 2H), 4.07 (s, 2H), 3.40 (t, J=6.00 Hz, 2H), 3.15-3.23 (m, 2H), 3.22 (s, 3H), 2.40 (s, 3H), 1.80 (quintet, J=6.27 Hz, 2H). $^{13}$C NMR (126 MHz, DMSO-$d_6$) δ 190.0, 171.2, 158.6, 151.1, 149.0, 148.9, 141.7, 131.0, 116.5, 113.7, 108.0, 104.9, 70.0, 58.4, 53.3, 45.9, 41.9, 29.0, 13.4. HRMS m/z: [M+H]$^+$ Calcd for $C_{19}H_{25}N_6O_4$ 401.1937; Found 401.1944.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A pharmaceutical composition comprising a therapeutically effective amount of a compound, or a pharmaceutically acceptable salt of the compound, and a pharmaceutically acceptable carrier, to treat a bacterial or protozoan infection, wherein the compound has the following structure:

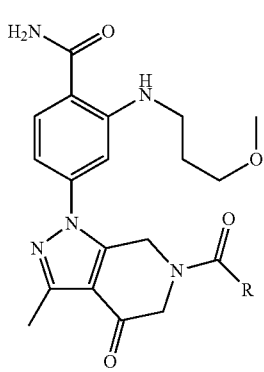

wherein R is NH$_2$, Me, Et, iPr, CH$_2$OMe, cyclopentyl, or p-tolyl.

2. The composition of claim 1, wherein the infection is at least one of: *Leishmania, Enterococcus faecium, Staphylococcus aureus, Klebsiella pneumoniae, Acinetobacter baumannii, Pseudomonas aeruginosa,* or *Enterobacter cloacae*.

3. A composition comprising a compound, wherein the compound has the following structure:

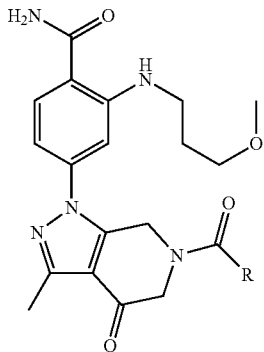

wherein R is NH$_2$, Me, Et, iPr, CH$_2$OMe, cyclopentyl, or p-tolyl.

4. A method of treating an infection comprising: delivering to a subject in need thereof, a pharmaceutical composition, wherein the pharmaceutical composition includes a therapeutically effective amount of a compound, or a pharmaceutically acceptable salt of the compound, and a pharmaceutically acceptable carrier, to treat the bacterial or protozoan, wherein the compound has the following structure:

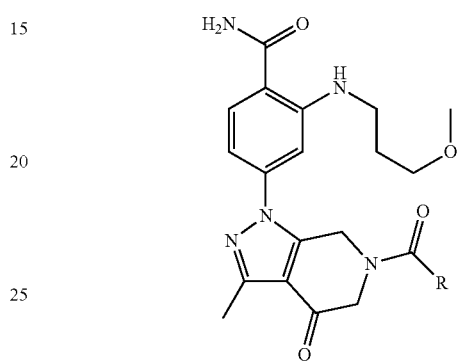

wherein R is NH$_2$, Me, Et, iPr, CH$_2$OMe, cyclopentyl, or p-tolyl.

5. The method of claim 4, wherein the infection is at least one of: *Leishmania, Enterococcus faecium, Staphylococcus aureus, Klebsiella pneumoniae, Acinetobacter baumannii, Pseudomonas aeruginosa,* or *Enterobacter cloacae*.

* * * * *